United States Patent
Frey et al.

(10) Patent No.: US 11,524,055 B2
(45) Date of Patent: Dec. 13, 2022

(54) METHODS FOR TREATING DISEASES MEDIATED BY ERBB4-POSITIVE PRO-INFLAMMATORY MACROPHAGES

(71) Applicant: Children's Hospital Los Angeles, Los Angeles, CA (US)

(72) Inventors: Mark R. Frey, Glendale, CA (US); Michael Schumacher, Glendale, CA (US)

(73) Assignee: Children's Hospital Los Angeles, Los Angeles, CA (US)

( * ) Notice: Subject to any disclaimer, the term of this patent is extended or adjusted under 35 U.S.C. 154(b) by 379 days.

(21) Appl. No.: 16/883,695

(22) Filed: May 26, 2020

(65) Prior Publication Data
US 2020/0353043 A1 Nov. 12, 2020

Related U.S. Application Data

(63) Continuation of application No. 15/764,239, filed as application No. PCT/US2016/054027 on Sep. 27, 2016, now Pat. No. 10,702,586.

(60) Provisional application No. 62/233,928, filed on Sep. 28, 2015.

(51) Int. Cl.
| | |
|---|---|
| *A61P 11/08* | (2006.01) |
| *A61P 3/10* | (2006.01) |
| *A61P 9/10* | (2006.01) |
| *A61P 1/00* | (2006.01) |
| *A61K 38/18* | (2006.01) |
| *G01N 33/50* | (2006.01) |
| *G01N 33/68* | (2006.01) |

(52) U.S. Cl.
CPC ............ *A61K 38/1883* (2013.01); *A61P 3/10* (2018.01); *A61P 9/10* (2018.01); *A61P 11/08* (2018.01); *A61P 1/00* (2018.01); *G01N 33/5005* (2013.01); *G01N 33/6893* (2013.01)

(58) Field of Classification Search
CPC ........ A61K 38/1883; A61P 9/10; A61P 11/08; A61P 3/10; A61P 1/00; G01N 33/5005; G01N 33/6893
See application file for complete search history.

(56) References Cited

U.S. PATENT DOCUMENTS

| | | | |
|---|---|---|---|
| 6,544,759 | B1 | 4/2003 | Harari et al. |
| 7,094,882 | B2 | 8/2006 | Harari et al. |
| 9,352,023 | B2 * | 5/2016 | Frey .................... G01N 33/573 |
| 10,716,830 | B2 | 7/2020 | Frey |
| 2002/0082229 | A1 | 6/2002 | Godowski et al. |
| 2008/0008711 | A1 | 1/2008 | Schleyer et al. |
| 2010/0239654 | A1 | 9/2010 | Winter |
| 2014/0178404 | A1 | 6/2014 | Frey |
| 2016/0317619 | A1 | 11/2016 | Frey |
| 2018/0271944 | A1 | 9/2018 | Frey et al. |
| 2018/0318391 | A1 | 11/2018 | Frey |
| 2020/0354421 | A1 | 11/2020 | Day et al. |

FOREIGN PATENT DOCUMENTS

| | | |
|---|---|---|
| EP | 2744512 A1 | 6/2014 |
| EP | 3355909 A1 | 8/2018 |
| EP | 3591398 A1 | 1/2020 |
| ES | 2745644 T3 | 3/2020 |
| HK | 1198932 A1 | 6/2015 |
| JP | 2017109987 A | 6/2017 |
| JP | 6912875 B2 | 8/2021 |
| WO | 2007014167 A2 | 2/2007 |
| WO | 2010060265 A1 | 6/2010 |
| WO | 2011006072 A1 | 1/2011 |
| WO | 2013025817 A1 | 2/2013 |
| WO | 2014153385 A1 | 9/2014 |
| WO | 2017058828 A1 | 4/2017 |

OTHER PUBLICATIONS

Hayes et al., Identification and Characterization of Novel Spliced Variants of Neuregulin 4 in Prostate Cancer, 2007, Clin Cancer Res, vol. 13(11), pp. 3147-3155.

Harari et al., Neuregulin-4: a novel growth factor that acts through the ErbB-4 receptor tyrosine kinase, 1999, Oncogene, vol. 18, pp. 2681-2689.

Hayes et al., Characterization of the cell membrane-associated products of the Neuregulin 4 gene, 2008, Oncogene, vol. 27, pp. 715-720.

EP 19176250.9 Extended European Search Report dated Nov. 22, 2019, 8 pages.

Mcelroy et al., Tumor Necrosis Factor Inhibits Ligand-Stimulated EGF Receptor Activation through a TNF Receptor 1-Dependent Mechanism, Am J Physiol Gastrointest Liver Physiol, 2008, vol. 295, pp. 285-293.

Treede et al., Anti-Inflammatory Effects of Phosphatidylcholine, The Journal of Biological Chemistry, 2007, vol. 282 (37), pp. 27155-27164.

Yan et al., Kinase Suppressor of Ras Determines Survival of Intestinal Epithelial Cells Exposed to Tumor Necrosis Factor, Cancer Research, 2001, vol. 61, pp. 8668-8675.

Wirtz, Chemically Induced Mouse Models of Intestinal Inflammation, 2007, Nature Protocols, vol. 2(3), pp. 541-546.

(Continued)

*Primary Examiner* — Timothy R Rozof

(74) *Attorney, Agent, or Firm* — Nixon Peabody LLP; Linda B. Huber

(57) ABSTRACT

Provided herein are methods and compositions for treating disease-states associated with presence of increased number of ErbB4+ pro-inflammatory macrophages in a subject in need thereof. The methods include providing an activator of ErbB4 and administering a therapeutically effective amount of the activator to the subject. The compositions include an activator of ErbB4. In one embodiment, the activation of ErbB4 is Neuregulin-4.

9 Claims, 16 Drawing Sheets

(56) References Cited

OTHER PUBLICATIONS

Yamasaki et al., Lung Macrophage Phenotypes and Functional Responses: Role in the Pathogenesis of COPD, 2018, Int. J. Mol. Sci., vol. 19(582), 12 Pages.

Yusta et al., ErbB Signaling is Required for the Proliferative Actions of GLP-2 in the Murine Gut, 2009, Gastroenterology, vol. 137, pp. 986-996.

Zhang et al., Kupffer Cells: Increasingly Significant Role in Nonalcoholic Fatty Liver Disease., 2014, Ann. Hepatol., vol. 13(5), pp. 489-495.

International Search Report and Written Opinion of PCT Application No. PCT/US2012/050970, dated Jan. 24, 2013, 9 Pages.

International Preliminary Report on Patentability of PCT Application No. PCT/US2012/050970, dated Feb. 27, 2014, 7 pages.

Extended Search Report of EP 12824129.6, dated May 4, 2017, 8 Pages.

International Search Report and Written Opinion of PCT Application No. PCT/US2016/054027, dated Feb. 21, 2017, 10 Pages.

International Preliminary Report on Patentability for Application No. PCT/US2016/054027, dated Apr. 3, 2018, 8 Pages.

Extended European Search Report of EP 16852432.0, dated Apr. 29, 2019, 5 Pages.

Aggarwal et al., Diverse Macrophage Populations Mediate Acute Lung Inflammation and Resolution, 2014, Am J Physiol Cell Mol Physiol, vol. 306, pp. L709-L725.

Baeck et al. Pharmacological Inhibition of the Chemokine C-C Motif Chemokine Ligand 2 (Monocyte Chemoattractant Protein 1) Accelerates Liver Fibrosis Regression by Suppressing Ly-6C+ Macrophage Infiltration in Mice., 2014, Hepatology vol. 59(3), pp. 1060-1072.

Bain et al., Resident and Pro-Inflammatory Macrophages in the Colon Represent Alternative Context-Dependent Fates of the Same Ly6Chi Monocyte Precursors., 2013, Mucosal Immunol vol. 6(3), pp. 498-510.

Barnes, P., Inflammatory Mechanisms in Patients with Chronic Obstructive Pulmonary Disease, 2016, Journal of Allergy and Clinical Immunology, vol. 138(1), pp. 16-27.

Bernard et al., Neuregulin-4 is a Survival Factor for Colon Epithelial Cells Both in Culture and in Vivo, 2012, The Journal of Biological Chemistry, vol. 287(47), pp. 39850-39858.

Blirando et al., Mast Cells Are an Essential Component of Human Radiation Proctitis and Contribute to Experimental Colorectal Damage in Mice., 2011, Am. J. Pathol., 2011, vol. 178(2), pp. 640-651.

Boerma et al. Orazipone, a Locally Acting Immunomodulator, Ameliorates Intestinal Radiation Injury: A Preclinical Study in a Novel Rat Model., 2006, Int. J. Radiat. Oncol. Biol. Phys., vol. 66(2), pp. 552-559.

Bueter et al. ErbB receptors in fetal endothelium—a potential linkage point for inflammation-associated neonatal disorders? Cytokine, Dec. 2006; vol. 36(5-6) pp. 267-275.

Eguchi et al., Macrophages and Islet Inflammation in Type 2 Diabetes, 2013, Diabetes Obes. Metab., vol. 15, Suppl 3, pp. 152-158.

Espinoza-Jimenez et al., Alternatively Activated Macrophages in Types 1 and 2 Diabetes, 2012, Mediators of Inflammation, Article ID 815953, 10 Pages.

Grainger et al., Macrophages in gastrointestinal homeostasis and inflammation, 2017, Pflugers Arch —Eur. J. Physiol., vol. 469(3-4), pp. 527-539.

Gregory et al., Macrophage Migration Inhibitory Factor Induces Macrophage Recruitment via CC Chemokine Ligand 2, 2006, J. Immunol., vol. 177(11): 8072-8079.

Guiteras et al., Macrophage in Chronic Kidney Disease, 2016, Clinical Kidney Journal, vol. 9(6), pp. 765-771.

Hayes et al., Innate Immune Responses to Bladder Infection., 2016, Microbiol. Spectr., vol. 4(6), 11 Pages.

Heinsbroek et al., The Role of Macrophages in Inflammatory Bowel Diseases, 2009, vol. 11, e14, 19 pages.

Hilliard et al. "TNF-[alpha] converting enzyme-mediated ErbB4 transactivation by TNF promotes colonic epithelial cell survival." Am J Physiol Gastrointest Liver Physiol. (2011). 301(2): G338-46.

Hovdenak et al., Acute Radiation Proctitis: a Sequential Clinicopathologic Study during Pelvic Radiotherapy., 2000, Int. J. Radiat. Oncol. Biol. Phys., vol. 48(4), pp. 1111-1117.

Hovdenak et al., Clinical Significance of Increased Gelatinolytic Activity in the Rectal Mucosa during External Beam Radiation Therapy of Prostate Cancer., 2002, Int. J. Radiat. Oncol. Biol. Phys., vol. 53(4), pp. 919-927.

Li et al., Hepatic Macrophages in Liver Fibrosis: Pathogenesis and Potential Therapeutic Targets., 2016, BMJ open Gastroenterol, vol. 3, e000079, 4 Pages.

Lissner et al., Monocyte and M1 Macrophage-induced Barrier Defect Contributes to Chronic Intestinal Inflammation in IBD., 2015, Inflamm. Bowel Dis., vol. 21(6), pp. 1297-1305.

Mahida YR, The Key Role of Macrophages in the Immunopathogenesis of Inflammatory Bowel Disease., 2000, Inflamm Bowel Dis, vol. 6(1), pp. 21-33.

Martin et al., Increased Expression of CCL2 in Insulin-Producing Cells of Transgenic Mice Promotes Mobilization of Myeloid Cells From the Bone Marrow, Marked Insulitis, and Diabetes, 2008, Diabetes, vol. 57(11), pp. 3025-3033.

Mcelroy et al., The ErbB4 Ligand Neuregulin-4 Protects against Experimental Necrotizing Enterocolitis, 2014, The American Journal of Pathology, vol. 184(10), pp. 2768-2778.

Mirzoeva et al., Single Administralion of p2TA (AB103), a CD28 Antagonist Peptide, Prevents Inflammatory and Thrombotic Reactions and Protects against Gastrointestinal Injury in Total-Body Irradiated Mice, 2014, PLoS One, vol. 9(7):e101161, 8 Pages.

Misharin et al., Monocyte-Derived Alveolar Macrophages Drive Lung Fibrosis and Persist in the Lung over the Life Span, 2017, J. Exp. Med., vol. 214(8), pp. 2387-2404.

Moore et al., Macrophages in Atherosclerosis: a Dynamic Balance, 2013, Nat Rev Immunol., vol. 13(10), pp. 709-721.

Naresh et al., The ERBB4/HER4 Intracellular Domain 4ICD is a BH3-Only Protein Promoting Apoptosis of Breast Cancer Cells, 2006, Cancer Research, vol. 66(12), pp. 6412-6420.

Ngo, et al. "Computational Complexity, Protein Structure Predition, and the Levintahl Paradox." In Merz and LeGran (Eds). The Protein Foiling and Tertiary Structure Predition. pp. 491-495, 1994, Birkhauser, Boston.

Paatero et al., ErbB4 and Its Isoforms: Patentable Drug Targets?, 2008, Recent Patents on DNA & Gene Sequences, vol. 2(1)., pp. 27-33.

Parisi et al., Macrophage Polarization in Chronic Inflammatory Diseases: Killers or Builders?, 2018, Journal of Immunology Research, vol. 2018, Article ID 8917804, 25 Pages.

Rannou et al., In Vivo Evidence for an Endothelium-Dependent Mechanism in Radiation-Induced Normal Tissue Injury, 2015, Scientific Reports, vol. 5(15738), 13 Pages.

Ren et al., Up-Regulation of Macrophage Migration Inhibitory Factor in Infants with Acute Neonatal Necrotizing Enterocolitis., 2005, Histopathology, 9 Pages.

Schumacher, et al. Macrophage-Specific ErbB4 is Induced by DSS Colitis and Regulates Macrophage Survival, Presentation on Mar. 30, 2015 at Experimental Biology 2015 Meeting Held at Boston Convention & Exhibit Center, 15 Pages.

Schumacher, et al. Macrophage-Expressed ErbB4 is Protective Against Colitis, Presentation on May 17, 2015 at DDW Conference, Held at Walter E. Washington Convention Center, 17 Pages.

Schumacher, et al. Macrophage-Specific ErbB4 is Induced by DSS Colitis and Regulates Macrophage Survival, Abstract Accessible online in The FASEB Journal for the Experimental Biology 2015 Meeting, 3 Pages.

Schumacher, et al. ErbB4 Expression on Macrophages is Induced by DSS Colitis and Negatively Regulates Macrophage Survival, Abstract published in Apr. 2015 in Gastroenterology for the Digestive Disease Week 2015 conference, 2 Pages.

Schumacher, et al. Neuregulin-4 Stimulates Pro-Inflammatory Macrophage Apoptosis Through ADAM17 Dependent Cleavage of ErbB4 to Ameliorate Colitis [retreive online Jan. 31, 2017 at

(56) References Cited

OTHER PUBLICATIONS http://www.gastrojournal.org/article/S0016-5085(16)30804-6/abstract Gastroenterology (Apr. 2016) vol. 150, Issue 4, Supplement 1, p. S217.
Sun et al. Macrophage Phenotype in Liver Injury and Repair., 2017, Scand. J. Immunol. vol. 85(3), pp. 166-174.
Swirski et al., Ly-6Chi Monocytes DominateHypercholesterolemia-Associated Monocytosisand Give Rise to Macrophages in Atheromata, 2007, J Clin Invest, vol. 117, pp. 195-205.
Vlahos et al., Role of Alveolar Macrophages in Chronic Obstructive Pulmonary Disease, 2014, Front. Immunol., vol. 5, Article 435, 7 Pages.
Wan et al., M2 Kupffer Cells Promote M1 Kupffer Cell Apoptosis: A Protective Mechanism against Alcoholic and Nonalcoholic Fatty Liver Disease., 2014, Hepatology, vol. 59(1), pp. 130-142.
Wang et al., The Brown Fat-Enriched Secreted Factor Nrg4 Preserves Metabolic Homeostatis through Attenuating Hepatic Lipogenesis, 2014, Nat. Med., vol. 20(12), pp. 1436-1443.
Wei et al., M1 to M2 Macrophage Polarization in HB-EGF Therapy for NEC, 2015, J. Surg. Res., vol. 197(1): 126-138.
Wells, "Additivity of Mutual Effects in Proteins". Biochemistry, vol. 29, No. 37, (1990) pp. 8509-8517, American Chemical Society.

\* cited by examiner

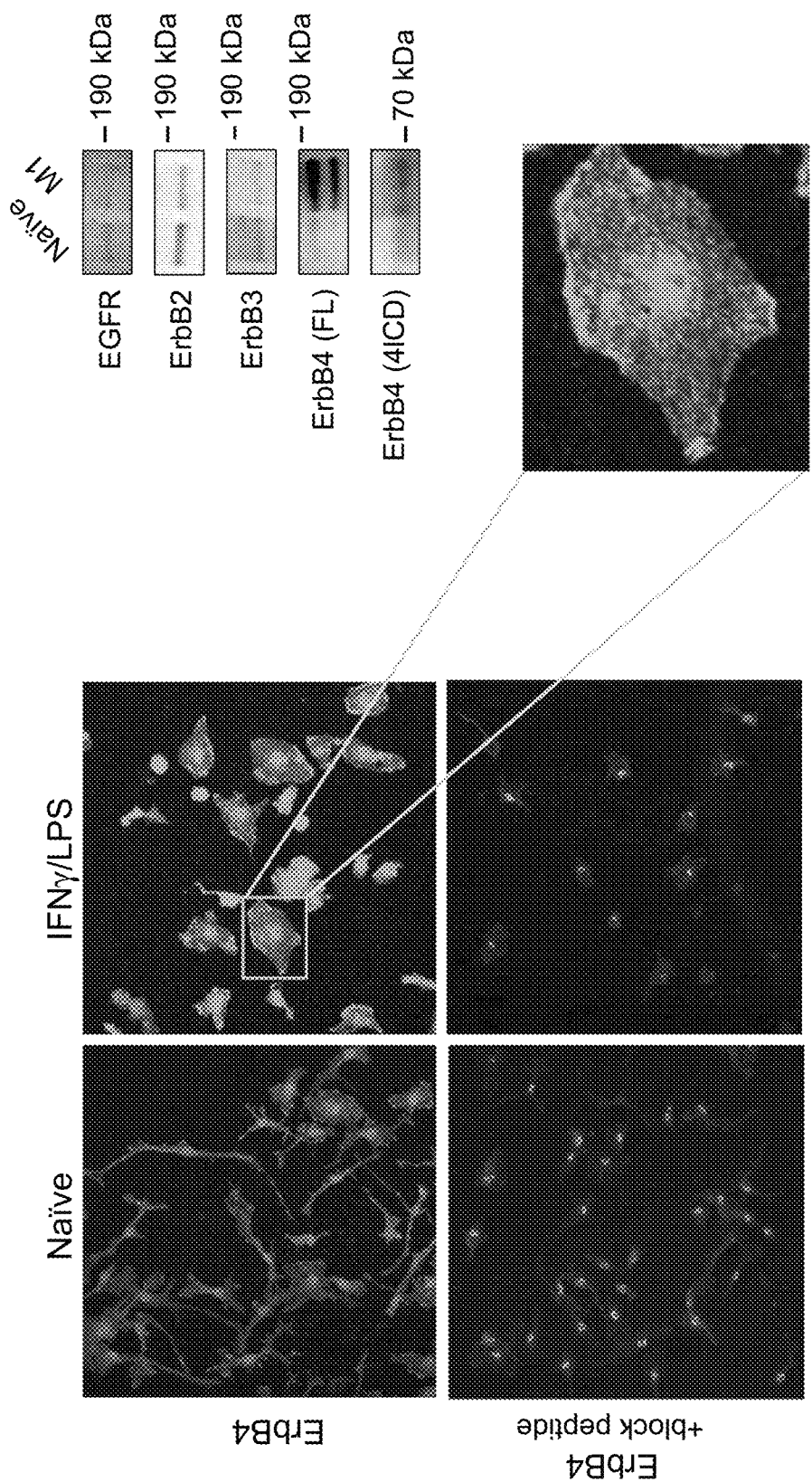

Viable macrophages after 48 hours

NRG4: 100 ng/ml
E4BA: 2 µg/ml

Active Caspase-3+ macrophages after 48 hours

NRG4: 100 ng/ml
E4BA: 2 µg/ml cCasp3 (red) staining of macrophages

M1          M1 +NRG4

NRG4 in colon post-DSS n=3-4 mice per group

LysMCre/ErbB4FF mice: Genetically lack ErbB4 in macrophages

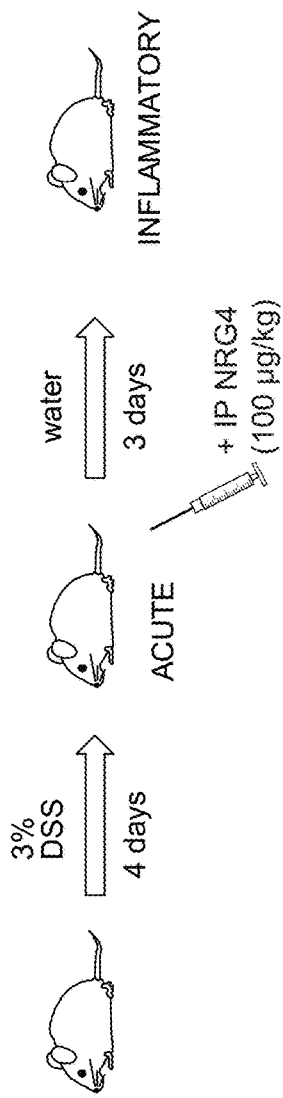
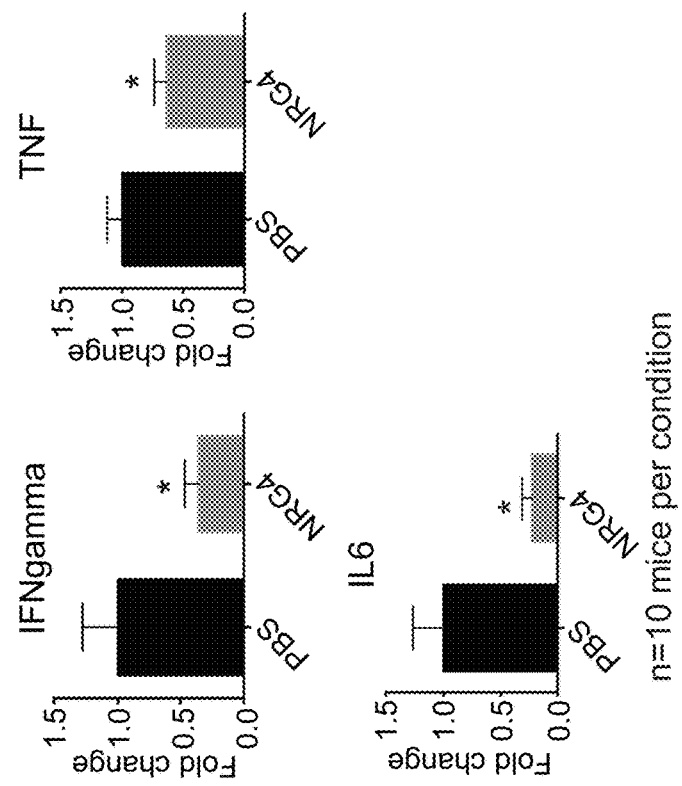
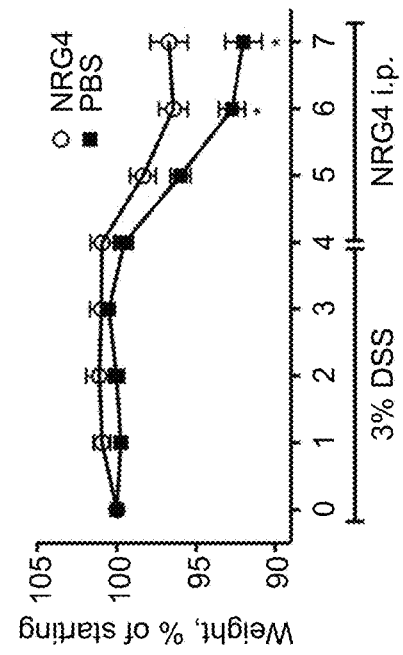
FIG. 6A
FIG. 6B
FIG. 6C

IP: PBS

IP: NRG4

POST-DSS F4/80$^{HI}$/CD11b$^{HI}$ COLONIC MACROPHAGES n=5 mice per condition

Blue, Nuclei; Green, F4/80; Red, ErbB4

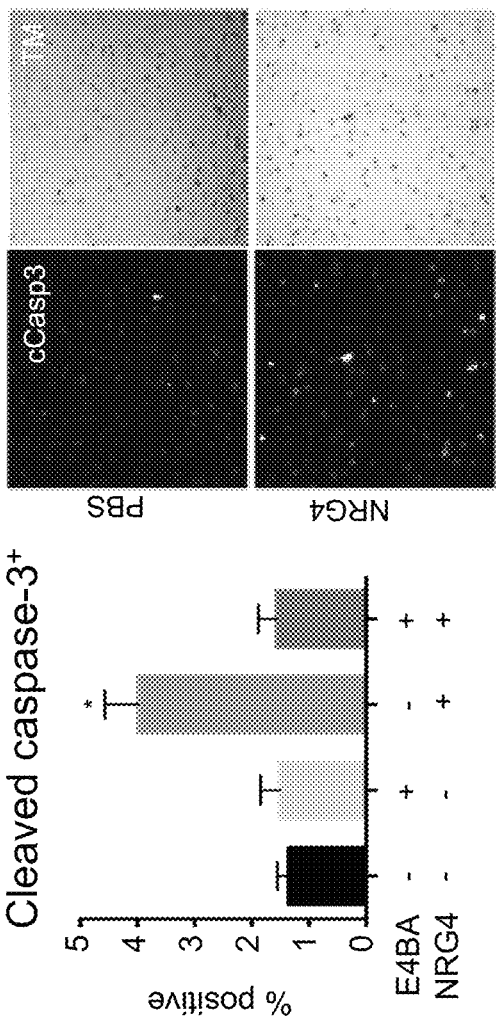
FIG. 8A
FIG. 8B
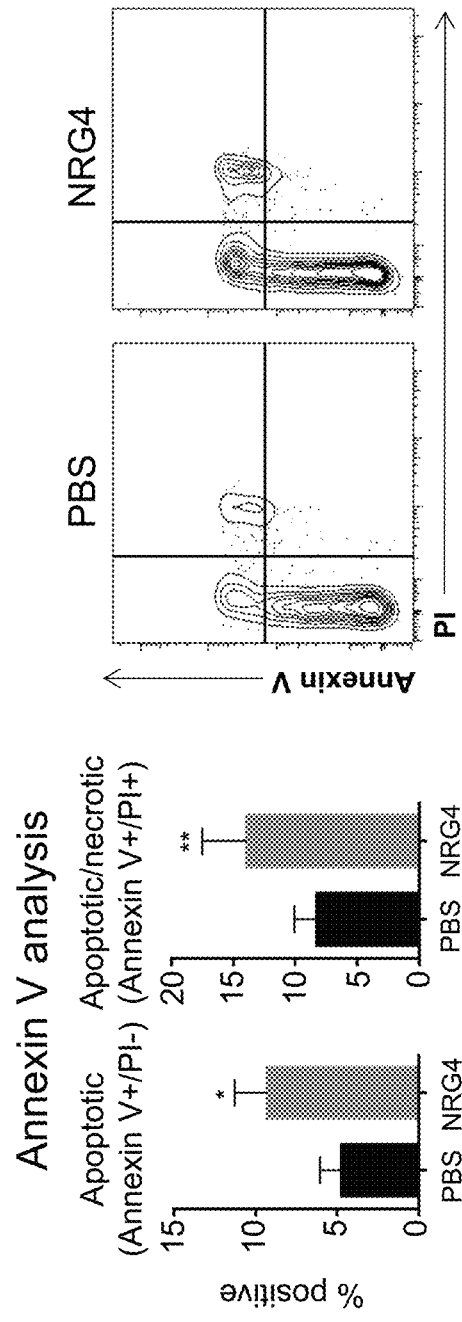
FIG. 8C

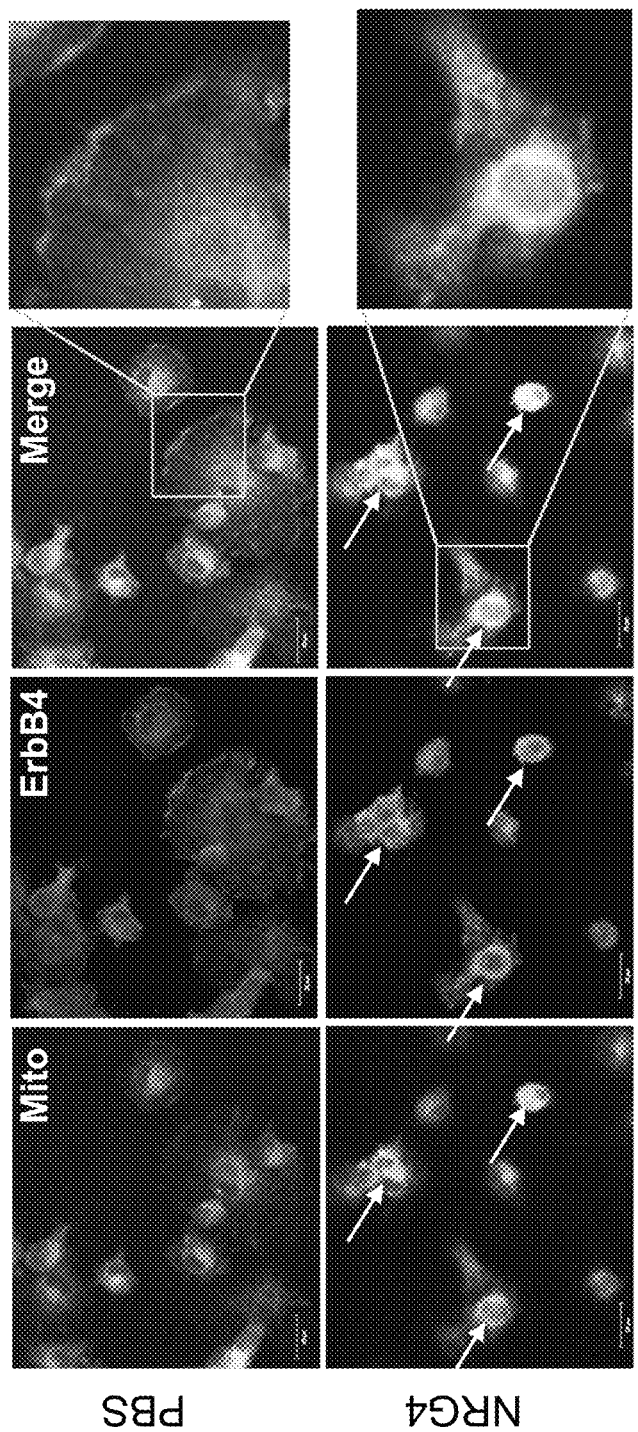

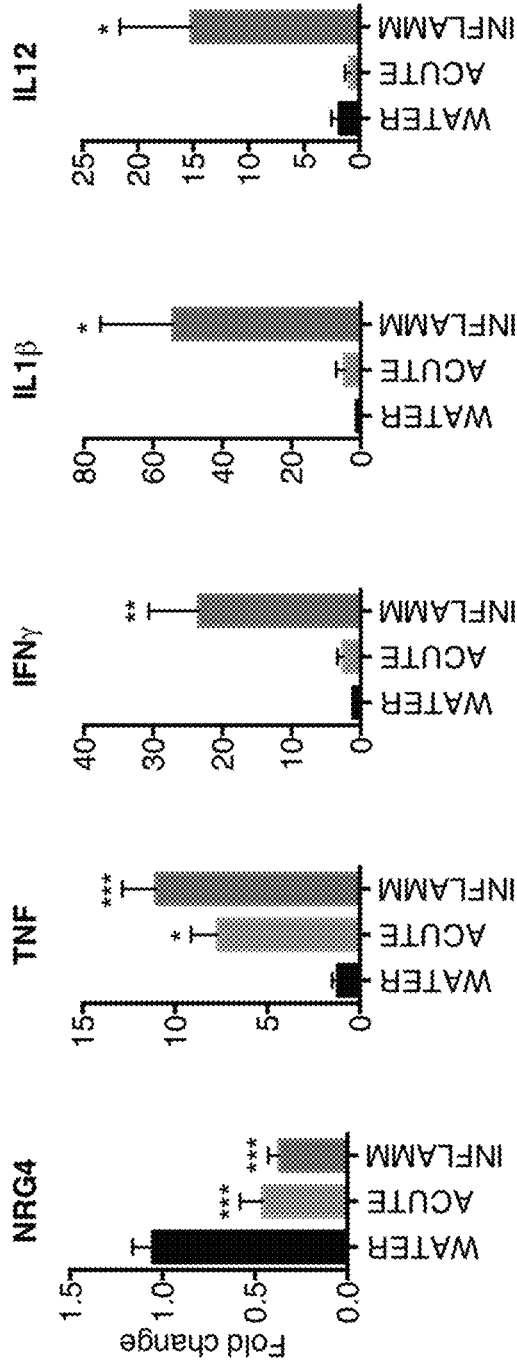
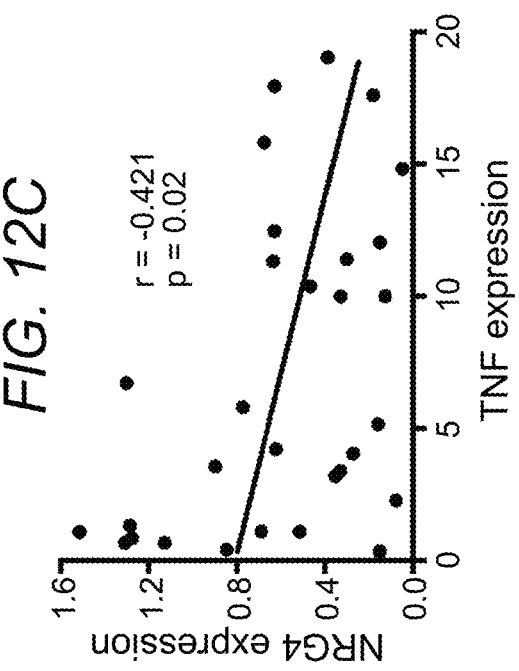
FIG. 12A
FIG. 12B
FIG. 12C

METHODS FOR TREATING DISEASES MEDIATED BY ERBB4-POSITIVE PRO-INFLAMMATORY MACROPHAGES

CROSS-REFERENCE TO RELATED APPLICATIONS

This application is a continuation of U.S. patent application Ser. No. 15/764,239, filed Mar. 28, 2018, now U.S. Pat. No. 10,702,586, which is a National Stage of International Application No. PCT/US2016/054027, filed Sep. 27, 2016, which designated the U.S. and that International Application was published under PCT Article 21(2) in English, which also includes a claim of priority under 35 U.S.C. § 119(e) to U.S. Provisional Patent Application No. 62/233,928, filed Sep. 28, 2015, now expired, the entirety of which is hereby incorporated by reference.

STATEMENT REGARDING FEDERALLY SPONSORED RESEARCH OR DEVELOPMENT

This invention was made with government support under Grant No. DK095004 awarded by the National Institutes of Health. The government has certain rights in the invention.

FIELD OF INVENTION

The invention provides methods for treating disease-states associated with increased number of ErbB4+ pro-inflammatory macrophages in a subject in need thereof using activators of ErbB4.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

ErbB4 is the least well-understood member of the family of receptor tyrosine kinases which also includes EGF receptor (EGFR/ErbB1), ErbB2/HER2, and ErbB3 (Wieduwilt, M. J., and Moasser, M. M. (2008) *Cellular and molecular life sciences: CMLS* 65, 1566-1584). ErbBs recognize and are activated by a suite of ligands including heparin-binding EGF-like growth factor (HB-EGF), betacellulin, and the heregulin/neuregulin family (Wilson, K. J., et al., 2nd. (2009) *Pharmacology & therapeutics* 122, 1-8). Ligand binding is associated with receptor dimerization, increased tyrosine kinase activity, and auto-phosphorylation on c-terminal tyrosine residues, which then provide docking sites for downstream effectors (Bublil, E. M., and Yarden, Y. (2007) *Current opinion in cell biology* 19, 124-134). Different ligands show distinct specificities and affinities for different ErbB receptors, and stimulate diverse dimerization patterns, signaling, and cellular responses (Saito, T. et al. (2004) *Endocrinology* 145, 4232-4243; Sweeney, C. et al., 3rd. (2000) *J Biol Chem* 275, 19803-19807).

ErbB4 has several features which distinguish it from other tyrosine kinases, making it a unique target both in terms of signaling and potential role in human disease. It can bind both heregulin/neuregulin growth factors and a subset of EGF-family factors (Jones, J. T., et al. (1999) *FEBS letters* 447, 227-231), but at least one peptide ligand—NRG4—is exclusive to ErbB4 and does not bind ErbB1-3 (Harari, D., et al. (1999) *Oncogene* 18, 2681-2689). Furthermore, ErbB4 associates with a divergent and more restricted suite of SH2-containing targets than EGFR, ErbB2, or ErbB3 (Kaushansky, A., et al. (2008) *Chem Biol* 15, 808-817). Thus, selective ErbB4 activation with NRG4 may elicit different cellular outcomes than stimulation with other EGF-like or heregulin family molecules.

ErbB4 is induced in colonic epithelial cells by inflammatory cytokines, and is present at elevated levels in the inflamed colonic mucosa of IBD patients (Frey, M. R., et al. (2009) *Gastroenterology* 136, 217-226). This appears to be a compensatory protective response rather than a pathological process, as ectopic ErbB4 overexpression protects cultured mouse colon epithelial cells from cytokine-induced apoptosis in a ligand-dependent manner (Frey, M. R. et al. (2009) *Gastroenterology* 136, 217-226; Hilliard, V. C., et al. (2011) *American journal of physiology. Gastrointestinal and liver physiology* 301, G338-346; Frey, M. R., et al. (2010) *Laboratory Investigation* 90, 1415-1424). However, these studies, like most investigation of ErbB4 function, used shared ErbB ligands heregulin (HRG)-1β or HB-EGF, raising the question of signal specificity.

As discussed above, the ErbB4 receptor tyrosine kinase is induced in the colonic epithelium in diseases such as inflammatory bowel disease (IBD), and the ErbB4-specific ligand neuregulin-4 is protective in murine colitis models. Interestingly, ErbB4 is also robustly detectable in the submucosal stroma where immune cells accumulate during inflammation. Previous studies have shown ErbB4 expression on circulating human monocytes and neuronal macrophages (Mø), but its expression on, for example, intestinal Mø, lung Mø, cardiac Mø, liver Mø etc. and role in Mø biology are unknown. As Mø play a significant role in the development of diseases, we hypothesized that receptor-mediated ErbB4 signaling may be an anti-inflammatory mechanism to limit Mø numbers during inflammation.

SUMMARY

ErbB4, in the presence of its activator Neuregulin-4 exhibits canonical signaling and promotes epithelial cell survival, epithelial cell proliferation, epithelial cell motility and preservation of epithelial cell integrity. As described herein, the inventors have identified a completely unique role of activated ErbB4 in pro-inflammatory macrophages. Specifically, polarization of macrophages to a pro-inflammatory state induces ErbB4 expression on the macrophages, and subsequent ErbB4 activation promotes apoptosis of these cells. This role for activated ErbB4 in promoting apoptosis of ErbB4+ pro-inflammatory macrophages has never before been described and is unexpected. Based on previous findings that NRG-4 prevents apoptosis of intestinal epithelial cells (Bernard J K, et al. (2012). Neuregulin-4 is a survival factor for colon epithelial cells both in culture and in vivo. *J. Biol. Chem.* 287(47):39850-8), this is indeed unpredicted. Accordingly, provided herein are methods for treating disease-states associated with increased number of ErbB4+ pro-inflammatory macrophages by using an activator on ErbB4 (such as Neuregulin-4).

Provided herein is a method for treating disease-states associated with presence of increased number of ErbB4+ pro-inflammatory macrophages in a subject in need thereof. The method comprises providing an activator of ErbB4 and administering a therapeutically effective amount of the activator to the subject so as to treat the disease-states.

In some embodiment, the pro-inflammatory macrophages are M1 macrophages and are ErbB4+.

In some embodiments, the disease-state is inflammatory bowel disease, necrotizing enterocolitis, acute lung injury, liver fibrosis, non-alcoholic steatohepatitis (NASH), chronic obstructive pulmonary disease, atherosclerosis, urinary tract infections, gastroenteritis, radiation therapy-induced intestinal injury or type I diabetes.

In one embodiment, the subject has an increased number of ErbB4+ pro-inflammatory macrophages relative to reference value.

In another embodiment, the subject has an increased number of ErbB4+ pro-inflammatory macrophages relative to reference value and has been diagnosed with IBD.

In a further embodiment, the subject has an increased number of ErbB4+ pro-inflammatory macrophages relative to reference value and has been diagnosed with necrotizing colitis.

In some embodiments, the activator of ErbB4 is a directed activator or an indirect activator of ErbB4. In exemplary embodiments, the activator of ErbB4 is selected from the group consisting of a small molecule, a polypeptide, a peptide, an antibody or a fragment thereof and a nucleic acid molecule. In one embodiment, the ErbB4 activator is Neuregulin-4 or a pharmaceutical equivalent, analog, derivative, mimetic or a salt thereof.

Also provided herein is a method for treating inflammatory bowel disease (IBD) in a subject diagnosed with IBD, wherein the subject has an increased number of ErbB4+ pro-inflammatory macrophages. The method comprises providing an activator of ErbB4 and administering a therapeutically effective amount of the activator to the subject so as to treat the IBD. In an embodiment, the ErbB4 activator is Neuregulin-4. In one embodiment, the pro-inflammatory macrophages are M1 macrophages and are ErbB4+.

Also provided herein is a method for treating necrotizing enterocolitis (NEC) in a subject diagnosed with NEC, wherein the subject has an increased number of ErbB4+ pro-inflammatory macrophages. The method comprises providing an activator of ErbB4 and administering a therapeutically effective amount of the activator to the subject so as to treat the NEC in the subject. In an embodiment, the ErbB4 activator is Neuregulin-4. In one embodiment, the pro-inflammatory macrophages are M1 macrophages and are ErbB4+.

Also provided herein is a method for treating inflammatory bowel disease (IBD) in a subject diagnosed with IBD, wherein the subject has an increased number of ErbB4+ pro-inflammatory macrophages. The method comprises providing an activator of ErbB4 and administering a therapeutically effective amount of the activator to the subject so as to treat the IBD in the subject. In an embodiment, the ErbB4 activator is Neuregulin-4. In one embodiment, the pro-inflammatory macrophages are M1 macrophages and are ErbB4+.

Also provided herein is a method for treating acute lung injury in a subject diagnosed with acute lung injury, wherein the subject has an increased number of ErbB4+ pro-inflammatory macrophages. The method comprises providing an activator of ErbB4 and administering a therapeutically effective amount of the activator to the subject so as to treat the acute lung injury in the subject. In an embodiment, the ErbB4 activator is Neuregulin-4. In one embodiment, the pro-inflammatory macrophages are M1 macrophages and are ErbB4+.

In various embodiments, the activator of ErbB4 is administered intravenously, intramuscularly, intraperitoneally, orally, by enema or via inhalation. In an embodiment, the effective amount of the activator of ErbB4 is an amount that induces apoptosis of ErbB4+ pro-inflammatory macrophages. The effective amount will be apparent to a person of skill in the art.

In some embodiments, an increase in number of ErbB4+ macrophages is an increase relative to a reference value. In one embodiment, the reference value is the mean or median number of ErbB4+ pro-inflammatory macrophages in a normal (i.e. healthy or control) subject. In another embodiment, the reference value is the mean or median number of ErbB4+ macrophages in subjects that have been diagnosed and successfully treated for the disease-state. In various embodiments, successful treatment includes any of 10%, 20%, 30%, 40%, 50%, 60%, 70%, 80%, 90%, 99% or 100% improvement in symptoms.

Also provided herein is a pharmaceutical composition for treating IBD in a subject that has increased number of ErbB4+ pro-inflammatory macrophages. The composition comprises an activator of ErbB4, in an amount to induce apoptosis of ErbB4+ pro-inflammatory macrophages.

Further provided herein is a pharmaceutical composition for treating necrotizing enterocolitis in a subject that has increased number of ErbB4+ pro-inflammatory macrophages. The composition comprises an activator of ErbB4, in an amount to induce apoptosis of ErbB4+ pro-inflammatory macrophages.

Also provided herein is a pharmaceutical composition for treating acute lung injury, COPD, type 1 diabetes or atherosclerosis. The composition comprises an activator of ErbB4.

In various embodiments of the pharmaceutical composition provided herein, the activator of ErbB4 is Neuregulin-4 or a pharmaceutical equivalent, analog, derivative, mimetic or a salt thereof.

Also provided herein is a medicament for reducing the number of ErbB4+ pro-inflammatory macrophages in a subject need thereof. The medicament comprises, consists of or consists essentially of an effective amount of an activator of ErbB4. In an embodiment, the activator of ErbB4 is Neuregulin-4, or Neuregulin-4 analog or Neuregulin-4 mimetic.

BRIEF DESCRIPTION OF FIGURES

Exemplary embodiments are illustrated in the referenced figures. It is intended that the embodiments and figures disclosed herein are to be considered illustrative rather than restrictive.

FIG. 1A-FIG. 1F depict, in accordance with an embodiment of the invention, that pro-inflammatory activation of macrophages in vitro induces ErbB4 expression. ErbB family member RNA expression was determined after 6 hours stimulation of (FIG. 1A) BMDMs classically activated with IFNγ/LPS, (FIG. 1B) BMDMs alternatively activated with IL-4, (FIG. 1C) BMDCs activated with IFNγ/LPS, (FIG. 1D) neutrophils activated with LPS. For A-D, n=4-6 independent experiments per group. ND, not detectable. (FIG. 1E) Immunofluorescence staining (representative of 3 independent experiments) of BMDMs for ErbB4 (red), nuclei (blue) with or without blocking peptide to primary antibody. (FIG. 1F) Western blot for EGFR, ErbB2, ErbB3, ErbB4 (full length, FL; intracellular domain, 4ICD) following no stimulation (naïve) or 24 hours classical activation (M1). Representative blot from n=4 independent experiments. Error bars represent SEM. *, $p<0.05$; , $p<0.01$; *, $p<0$.

FIG. 6A-FIG. 6D depict, in accordance with an embodiment of the invention, that NRG4 treatment during macrophage-influx ameliorates colitis.

FIG. 8A-FIG. 8C depicts, in accordance with an embodiment of the invention, that NRG4 induces apoptosis in pro-inflammatory murine macrophages. (FIG. 8A) Classically activated (M1) or alternatively activated (M2) BMDMs were treated with NRG4 (100 ng/ml) for 48 hours and analyzed by resazurin-based cell titer assay to assess cell numbers compared to control. (FIG. 8B) Classically activated BMDMs pre-incubated for 30 minutes with or without 2 µg/ml ErbB4 neutralizing antibody (E4BA), and treated with or without NRG4 (100 ng/ml) for 48 hours, were stained for cleaved caspase-3. TM, transmitted light images of cultures. (FIG. 8C) Classically activated BMDMs treated with NRG4 (100 ng/ml) for 48 hours were stained for annexin V and propidium iodide (PI), and analyzed by flow cytometry to determine apoptotic cells. n=3-6 independent experiments for each panel. Error bars represent SEM. *, $p<0.05$; **, $p<0.01$.

FIG. 9A-FIG. 9C depicts, in accordance with an embodiment of the invention, that the metalloprotease TACE/ADAM17 and γ-secretase are necessary for NRG4-induced macrophage apoptosis. (FIG. 9A) Schematic model of potential ErbB4 signaling in macrophages following ligand binding. Step 1) Extracellular receptor cleavage by ADAM17; Step 2) intracellular cleavage by γ-secretase and generation of ErbB4 intracellular domain (4ICD); Step 3) migration of the active signaling fragment 4ICD to various intracellular compartments. (FIG. 9B) Classically activated BMDMs were pre-treated for 1 hour with metalloprotease inhibitor (GM6001, 10 γ-secretase inhibitor (DAPT, 10 or ADAM17 inhibitor (GW280264X, 3 µM) followed by 100 ng/ml NRG4 and 100 ng/ml LPS. Percent cell viability was analyzed by rezasurin-based cell titer assay. Error bars represent SEM. ***, $p<0.001$. (FIG. 9C) Immunofluorescence analysis of ErbB4 localization to the mitochondria of classically activated BMDMs treated with or without NRG4 (100 ng/ml) for 48 hours. Arrows point to representative cells with ErbB4/mitochondrial overlap. n=4 independent experiments.

(FIG. 10A) Human monocyte-derived macrophages were non-polarized (M0), classically activated (M1), or alternatively activated (M2) (n=8 donors), collected at the indicated time points, and stained/analyzed for ErbB4 expression by flow cytometry; representative flow plots and mean fluorescence intensity (MFI) of protein expression are shown. (FIG. 10B) Classically activated human macrophages (n=8 donors) were transfected with siRNA for ErbB4 and treated with 100 ng/ml LPS+ the indicated concentrations of NRG4 for 48 hours, and analyzed by flow cytometry for annexin V staining as a measure of apoptosis (n=8 donors). NRG4 treatment was initiated 72 hours after M1 polarization at peak ErbB4 expression. Significance was calculated compared to scr siRNA-transfected, untreated cells or as indicated. (FIG. 10C) ErbB4 knockdown was verified by flow cytometry (n=8 donors). Error bars represent SEM. *, $p<0.05$; , $p<0.01$; *, $p<0.001$; †, $p<1\times10-4$; ††, $p<1\times10-5$.

(FIG. 11A) Colonic mucosa from mice subjected to DSS colitis were analyzed by flow cytometry to determine percent of cells that are ErbB4+. Representative flow cytometric plots of the ErbB4+ population are shown for mice receiving no DSS (WATER), after 4 days of 3% DSS (INJURY), and after 4 days 3% DSS followed by 3 days without DSS (INFLAM). (FIG. 11B) Analysis of F4/80+/CD11b+ macrophages as a proportion of total mucosal cellularity at indicated time points. (FIG. 11C) Ly6C+/ErbB4+ and Ly6C-/ErbB4+ populations were analyzed. For total figure, n=9-10 mice per group from 3 independent DSS colitis experiments. Error bars represent SEM. *, $p<0.05$; , $p<0.01$; *, $p<0.001$.

FIG. 12A-FIG. 1211 depict, in accordance with an embodiment of the invention, that administration of the ErbB4 ligand NRG4 ameliorates inflammation and reduces colonic macrophage numbers. (FIG. 12A) Pro-inflammatory cytokine levels in colonic homogenates from mice subjected to acute DSS colitis were analyzed by qPCR. (FIG. 12B) Correlation, r, and p-value for expression of NRG4 and each cytokine. n=10 mice per condition in 3 independent experiments. (FIG. 12C) Correlation plot between relative NRG4 and TNF levels in all mice.

DETAILED DESCRIPTION

Figure 1A:
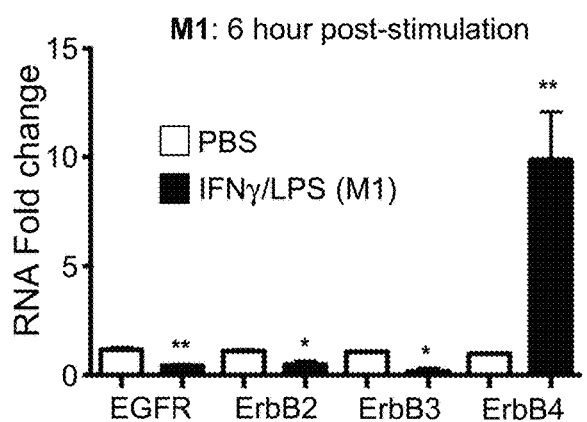

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013);

Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

For references on pediatrics, see Schwartz et al., *The 5-Minute Pediatric Consult* 4th ed., Lippincott Williams & Wilkins, (Jun. 16, 2005); Robertson et al., *The Harriet Lane Handbook: A Manual for Pediatric House Officers* 17th ed., Mosby (Jun. 24, 2005); and Hay et al., *Current Diagnosis and Treatment in Pediatrics* (*Current Pediatrics Diagnosis & Treatment*) 18th ed., McGraw-Hill Medical (Sep. 25, 2006).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. Beneficial or desired clinical results include, but are not limited to, alleviation of one or more symptom(s), diminishment of extent of the deficit, stabilized (i.e., not worsening) state of disease progression, delay or slowing of metastasis or invasiveness, and amelioration or palliation of symptoms associated with the disease. Treatment also includes a decrease in mortality or an increase in the lifespan of a subject as compared to one not receiving the treatment.

As used herein, the term "administering," refers to the placement an agent as disclosed herein into a subject by a method or route which results in at least partial localization of the agents at a desired site.

The term "sample" or "biological sample" as used herein denotes a sample taken or isolated from a biological organism, e.g., a fluid sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; tissue sample; tumor sample; and/or tumor biopsy etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

A subject can be one who has been previously diagnosed with or identified as suffering from or having a disease-state in need of monitoring (e.g., cancer or infectious disease) or one or more complications related to such a disease-state, and optionally, have already undergone treatment for the disease-state or the one or more complications related to the disease/condition. Alternatively, a subject can also be one who has not been previously diagnosed as having a disease-state or one or more complications related to the disease/condition. For example, a subject can be one who exhibits one or more risk factors for a disease-state or one or more complications related to a disease-state or a subject who does not exhibit risk factors. A "subject in need" of treatment for a particular disease-state can be a subject having that disease/condition, diagnosed as having that condition, or at risk of developing that disease.

The term "effective amount" as used herein refers to the amount of a pharmaceutical composition comprising one or more peptides as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the ErbB4 activator (such as Neuregulin-4). Measured or measurable parameters include clinically detectable markers of disease, for example, elevated or depressed levels of a biological marker, as well as parameters related to a clinically accepted scale of symptoms or markers for fibrosis and/or inflammation. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder, such as fibrosis (of the liver or lung), IBD, acute liver injury, COPD, atherosclerosis, radiation therapy-induced intestinal injury or diabetes. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

"Inflammatory Bowel Disease" or "IBD" as used herein refers to the inflammatory conditions including but not limited to Crohn's disease and ulcerative colitis. In addition to IBD, other inflammatory conditions of the intestine that may be targeted by activator of ErbB4 (such as Neuregulin-4) include Necrotizing Enterocolitis, collagenous colitis, lymphocytic colitis, ischaemic colitis, diversion colitis, Behçet's disease, gastroenteritis and indeterminate colitis.

As used herein "ErbB4+ pro-inflammatory macrophages" refer to pro-inflammatory macrophages that express ErbB4. Mφ as used herein refers to macrophages.

As used herein "ErbB4+ macrophages" macrophages refer to macrophages that express ErbB4 and are pro-inflammatory macrophages.

As used herein, "medicament" refers to pharmaceutical compositions or compositions.

Efficient clearance of pro-inflammatory macrophages from tissue after resolution of a challenge is critical to prevent prolonged inflammation. Defects in clearance can contribute to conditions such as inflammatory bowel disease, and thus may be therapeutically targetable. However, the signaling pathways that induce termination of pro-inflammatory macrophages are incompletely defined. We tested whether the ErbB4 receptor tyrosine kinase, previously not known to play a role in macrophage biology, is involved in this process. In vitro, pro-inflammatory activation of cultured murine and human macrophages induced ErbB4 expression; in contrast, other ErbB family members were not induced in pro-inflammatory cells, and other innate immune lineages (dendritic cells, neutrophils) did not express detectable levels of ErbB4. Treatment of activated pro-inflammatory macrophages with the ErbB4 ligand neuregulin-4 (NRG4) induced apoptosis. ErbB4 localized to the mitochondria in these cells, and apoptosis was dependent upon the proteases that generate the cleaved ErbB4 intracellular domain fragment, suggesting a requirement for this fragment and mitochondrial pathway apoptosis. In vivo, ErbB4 was highly expressed on pro-inflammatory macrophages during experimental DSS colitis in C57Bl/6 mice. Active inflammation in this model suppressed NRG4 expression, which may allow for persistence of macrophages and ongoing inflammation. Consistent with this notion, administration of exogenous NRG4 during colitis reduced colonic macrophage numbers and ameliorated inflammation. These data define a novel role for ErbB4 in macrophage apoptosis, and outline a mechanism of feedback inhibition that may promote resolution of colitis. Without wishing to be bound by a specific theory, the inventor hypothesizes that signaling through ErbB4 functions as an anti-inflammatory inhibitory feedback mechanism reducing inflammatory Mφ survival and/or function. A corollary of this hypothesis is that ErbB4 on pro-inflammatory Mφ promotes resolution of colitis and thus is a potential therapeutic target in IBD.

Therapeutic Methods

Accordingly, provided herein are methods for treating, inhibiting, reducing the symptoms of and/or promoting prophylaxis of disease-states associated with presence of increased number of ErbB4$^+$ Mφ. The methods include providing an ErbB4 activator and administering to the subject, an effective amount of the activator so as to treat, inhibit, reduce the symptoms of and/or promote prophylaxis of the disease-states. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the disease-state is inflammatory bowel disease, necrotizing enterocolitis, acute lung injury, liver fibrosis, non-alcoholic steatohepatitis (NASH), COPD, atherosclerosis or type I diabetes. In an embodiment, the presence of an increased number of ErbB4$^+$ Mφ is relative to a reference value.

Also provided herein are methods treating, inhibiting, reducing the symptoms of and/or promoting prophylaxis of inflammatory bowel disease in subjects with presence of increased number of ErbB4$^+$ Mφ with increased expression of ErbB4$^+$ Mφ. The methods include providing an ErbB4 activator and administering to the subject, an effective amount of the activator so as to treat, inhibit, reduce the symptoms of and/or promote prophylaxis of inflammatory bowel disease in subjects with increased expression of ErbB4$^+$ Mφ. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing treatments for inflammatory bowel disease. For example, ErbB4 activators may be used in conjunction with existing therapies such as diet modifications and administrations of therapeutic drugs including but not limited to sulfasalazine (Azulfadine), mesalamine (Asacol, Pentasa), azathioprine (Imuran), 6-MP (Purinethol), cyclosporine, methotrexate, infliximab (Remicade), Budesonide (Entocort EC) and corticosteroids (prednisone), so as to treat inflammatory bowel disease. Dosages of existing therapies that may be used with the ErbB4 activators will be apparent to one skilled in the art. In one embodiment, the ErbB4 activator (for example, Neuregulin-4) and existing therapies for IBD may be administered sequentially. In another embodiment, the ErbB4 activator (for example, Neuregulin-4) and existing therapies for IBD may be administered simultaneously.

Further provided herein is a method for treating, inhibiting, reducing the symptoms of and/or promoting prophylaxis of necrotizing enterocolitis in subjects with presence of increased number of ErbB4$^+$ Mφ. The methods include providing an ErbB4 activator and administering to the subject, an effective amount of the activator so as to treat, inhibit, reduce the symptoms of and/or promote prophylaxis of necrotizing enterocolitis in subjects with increased expression of ErbB4$^+$ Mφ. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing treatments for necrotizing enterocolitis including but not limited to stopping enteral feedings, performing nasogastric decompression, initiating broad-spectrum antibiotics, IV fluid support and surgery. (Sharma, R and Hudak, M. *Clin Perinatol.* 2013 March; 40(1): 27-51; Kasivajjula H and Maheshwari A. *Indian J Pediatr.* 2014 May; 81(5):489-97). In one embodiment, the ErbB4 activator (for example, Neuregulin-4) and existing therapies for necrotizing enterocolitis may be administered sequentially. In another embodiment, the ErbB4 activator (for example, Neuregulin-4) and existing therapies for necrotizing enterocolitis may be administered simultaneously.

Also provided herein are methods treating, inhibiting, reducing the symptoms of and/or promoting prophylaxis of radiation therapy-induced intestinal injury in a subject in need thereof. The methods include providing an ErbB4 activator and administering to the subject, an effective amount of the activator so as to treat, inhibit, reduce the symptoms of and/or promote prophylaxis of radiation therapy-induced intestinal injury in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof.

Also provided herein are methods treating, inhibiting, reducing the symptoms of and/or promoting prophylaxis of acute lung injury (ALI) in a subject in need thereof. The methods include providing an ErbB4 activator and administering to the subject, an effective amount of the activator so as to treat, inhibit, reduce the symptoms of and/or promote prophylaxis of ALI in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing or potential (new) treatments for ALI. For example, ErbB4 activators may be used in conjunction with existing therapies including ventilatory and non-ventilatory therapies. Additional treatments for ALI may include but are not limited to the use of statins, bone-marrow derived mesenchymal stem cells, aerosol therapies, corticosteroids, beta-adrenergic agonists and vasodilators (Jain R, DalNogare A. Pharmacological therapy for acute respiratory distress syndrome. *Mayo Clin Proc.* 2006; 81:205-212; Groshaus H E, Manocha S, Walley K R, Russell J A. Mechanisms of beta-receptor stimulation-induced improvement of acute lung injury and pulmonary edema. *Crit Care.* 2004; 8:234-242; Wheeler A P, Bernard G R. Acute lung injury and the acute respiratory distress syndrome: a clinical review. *Lancet.* 2007; 369:1553-1564; Johnson, E. and Matthay, M. *J Aerosol Med Pulm Drug Deliv.* 2010 August; 23(4): 243-252; Sweeney R M et al., *Semin Respir Crit Care Med.* 2013 August; 34(4):487-98). In one embodiment, the ErbB4 activator (for example, Neuregulin-4) and existing therapies for ALI may be administered sequentially. In another embodiment, the ErbB4 activator (for example, Neuregulin-4) and existing therapies for ALI may be administered simultaneously.

Also provided herein are methods treating, inhibiting, reducing the symptoms of and/or promoting prophylaxis of liver fibrosis in a subject in need thereof. The methods include providing an ErbB4 activator and administering to the subject, an effective amount of the activator so as to treat, inhibit, reduce the symptoms of and/or promote prophylaxis of liver fibrosis in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing treatments for liver fibrosis including but not limited to dietary modification, lifestyle changes, antifibrotic drugs, anti-inflammatory agents and antioxidants (Bataller, R. and Brenner, D. *J Clin Invest.* 2005 Feb. 1 115(2): 209-218; Detlef Schuppan and Yong Ook Kim. Evolving therapies for liver fibrosis. *J Clin Invest.* 2013; 123(5):1887-1901). In one embodiment, the ErbB4 activator (for example, Neuregulin-4) and existing therapies for liver fibrosis may be administered sequentially. In another embodiment, the ErbB4 activator (for example, Neuregulin-4) and existing therapies for liver fibrosis may be administered simultaneously.

Also provided herein are methods treating, inhibiting, reducing the symptoms of and/or promoting prophylaxis of non-alcoholic steatohepatitisin (NASH) a subject in need thereof. The methods include providing an ErbB4 activator and administering to the subject, an effective amount of the activator so as to treat, inhibit, reduce the symptoms of and/or promote prophylaxis of non-alcoholic steatohepatitis in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing treatments for non-alcoholic steatohepatitis including but not limited to dietary modification, lifestyle changes, lowering total cholesterol levels (for example, by using statins), weight loss, exercise, reduction or stoppage of alcohol consumption or combinations thereof. In one embodiment, the ErbB4 activator (for example, Neuregulin-4) and existing therapies for NASH may be administered sequentially. In another embodiment, the ErbB4 activator (for example, Neuregulin-4) and existing therapies for NASH may be administered simultaneously.

Also provided herein are methods treating, inhibiting, reducing the symptoms of and/or promoting prophylaxis of chronic obstructive pulmonary disease (COPD) in a subject in need thereof. The methods include providing an ErbB4 activator and administering to the subject, an effective amount of the activator so as to treat, inhibit, reduce the symptoms of and/or promote prophylaxis of COPD in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing treatments for COPD including but not limited to dietary modification, lifestyle changes, short-acting bronchodilators, long-acting bronchodilators, phosphodiesterase-4 (PDE4) inhibitors (such as roflumilast), corticosteroids and methylxanthines (Hobart L., Jeffrey, K. and Karine, T. Treatment of Stable Chronic Obstructive Pulmonary Disease: the GOLD Guidelines. *Am Fam Physician.* 2013 Nov. 15; 88(10):655-663). In one embodiment, the ErbB4 activator (for example, Neuregulin-4) and existing therapies for COPD may be administered sequentially. In another embodiment, the ErbB4 activator (for example, Neuregulin-4) and existing therapies for COPD may be administered simultaneously.

Also provided herein are methods treating, inhibiting, reducing the symptoms of and/or promoting prophylaxis of atherosclerosis in a subject in need thereof. The methods include providing an ErbB4 activator and administering to the subject, an effective amount of the activator so as to treat, inhibit, reduce the symptoms of and/or promote prophylaxis of atherosclerosis in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing treatments for atherosclerosis including but not limited to dietary modification, lifestyle changes, statins, anti-platelet medications, beta blocker medications, antiotensin-converting enzyme (ACE) inhibitors, calcium channel blockers, PCSK9 inhibitors, (Tabas, I. et al. Recent insights into the cellular biology of atherosclerosis. Apr. 13, 2015. *The Journal of Cell Biology* vol 209/no. 1, pg 13-22; Weber, C. and Noels, H. Atherosclerosis: current pathogenesis and therapeutic options. *Nature Medicine* Vol. 17, pg. 1410-1422 (2011). In one embodiment, the ErbB4 activator (for example, Neuregulin-4) and existing therapies for atherosclerosis may be administered sequentially. In another embodiment, the ErbB4 activator (for example, Neuregulin-4) and existing therapies for atherosclerosis may be administered simultaneously.

Also provided herein are methods treating, inhibiting, reducing the symptoms of and/or promoting prophylaxis of diabetes in a subject in need thereof. The methods include providing an ErbB4 activator and administering to the subject, an effective amount of the activator so as to treat, inhibit, reduce the symptoms of and/or promote prophylaxis of diabetes in the subject. In an embodiment, diabetes is Type I diabetes. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In various embodiments, the ErbB4 activator (for example, Neuregulin-4) may be used in conjunction with existing treatments for type I diabetes including but not limited to dietary modification, lifestyle changes, and insulin therapy (Chiang, J et al. Type 1 Diabetes Through the Life Span: A Position Statement of the American Diabetes Association. *Diabetes Care* July 2014 vol. 37 no. 7, pg. 2034-2054). In one embodiment, the ErbB4 activator (for example, Neuregulin-4) and existing therapies for type I diabetes may be administered sequentially. In another embodiment, the ErbB4 activator (for example, Neuregulin-4) and existing therapies for type I diabetes may be administered simultaneously.

In various embodiments of the methods described herein, the reference value is the mean or median number of ErbB4$^+$ macrophages in a normal (i.e. healthy or control) subject. In a further embodiment, the reference value is the mean or median number of ErbB4$^+$ macrophages in subjects that have been diagnosed with a disease-state and the subjects are undergoing or have undergone treatment for said disease-state. In exemplary embodiments, the ErbB4+ pro-inflammatory Mɸ in subject with disease-states relative to the reference value is increased by at least or about 10%, 20%, 30%, 40%, 50%, 60%, 70%, 80%, 90% or 100%. In exemplary embodiments, the ErbB4$^+$ pro-inflammatory Mɸ in subject with disease-states relative to the reference value is increased by at least or about 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

Also provided herein is a method for inducing cell death of ErbB4$^+$ Mɸ in a subject in need thereof. The methods include providing an ErbB4 activator and administering to the subject, an effective amount of the activator so as to induce cell death of ErbB4$^+$ Mɸ in the subject. In some embodiments, the activator of ErbB4 is selected from the group consisting of a small molecule, a peptide, an antibody or a fragment thereof and a nucleic acid molecule. In one embodiment, the ErbB4 activator is Neuregulin-4 or a pharmaceutical equivalent, analog, derivative, mimetic or a salt thereof. In one embodiment, the subject has IBD. In a further embodiment, the subject has necrotizing enterocolitis. In another embodiment, the subject has acute lung injury. In a further embodiment, the subject has liver fibrosis. In another embodiment, the subject has atherosclerosis. In a further embodiment, the subject has chronic obstructive pulmonary disease (COPD). In an additional embodiment, the subject has type I diabetes.

In some embodiments, the activator of ErbB4 is a direct activator of ErbB4 such that the activator binds ErbB4 and activates it by, for example, inducing or increasing phosphorylation of ErbB4. In some embodiments, the activator of ErbB4 is an indirect activator of ErbB4 such that the activator inhibits the inhibitor of ErbB4 so that ErbB4 is activated. In one embodiment, the ErbB4 activator is Neuregulin-4.

Also provided herein are assays for assessing the efficacy of treatment of disease-states associated with an increase in the number of ErbB4⁺ Mϕ, wherein the subject is undergoing or has undergone treatment with an activator of ErbB4. The assays include obtaining a sample from the subject; assaying the sample to determine the levels of ErbB4⁺ Mϕ in the sample; and determining that the treatment is effective if the level of the ErbB4⁺ Mϕ is decreased relative to a reference value or determining that the treatment is ineffective if the level of the ErbB4⁺ Mϕ is unchanged or increased relative to the reference value. In one embodiment, the reference value is the level of ErbB4⁺ Mϕ in the subject before starting treatment. In one embodiment, the treatment is determined to be effective if the levels of ErbB4⁺ Mϕ in the sample from the subject is similar to levels of ErbB4⁺ Mϕ in the reference value wherein the reference value is the level of ErbB4⁺ Mϕ in a normal (for example, healthy) subject. In one embodiment, the disease-state is IBD. In a further embodiment, the disease-state is necrotizing enterocolitis. In another embodiment, the disease-state is acute lung injury. In a further embodiment, the disease-state is liver fibrosis. In another embodiment, the disease-state is atherosclerosis. In a further embodiment, the disease-state is chronic obstructive pulmonary disease (COPD). In an additional embodiment, the disease-state is type I diabetes.

Various methods may be utilized to administer the ErbB4 activator for use with the claimed methods, including but not limited to aerosol, nasal, oral, transmucosal, transdermal, parenteral, sub-lingual, implantable pump, continuous infusion, topical application, enema, capsules and/or injections. In some embodiments, the disease-state is NEC or IBD and the ErbB4 activator is administered orally. In some embodiments, the disease-state is acute lung injury and the mode of administration of the ErbB4 activator is an aerosol.

The subjects treated by the present invention include mammalian subjects, including, human, monkey, ape, dog, cat, cow, horse, goat, pig, rabbit, mouse and rat.

Therapeutic Dosages

In some embodiments of the invention, the effective amount of ErbB4 activator in the composition can be in the range of about 1-10 mg/day, 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day. In one embodiment of the invention, the ErbB4 is Neuregulin-4 or a pharmaceutical equivalent, analog, derivative, mimetic or a salt thereof.

In further embodiments of the invention, the effective amount of activator of ErbB4 for use with the claimed methods may be in the range of 0.001-0.005 mg/kg, 0.005-0.01 mg/kg, 0.01-0.02 mg/kg, 0.02-0.04 mg/kg, 0.04-0.06 mg/kg, 0.06-0.08 mg/kg, 0.08-1 mg/kg, 1-5 mg/kg, 5-10 mg/kg, 5-7 mg/kg, 6-7 mg/kg, 6-8 mg/kg, 7-8 mg/kg. 7-10 mg/kg, 10-15 mg/kg, 15-20 mg/kg, 20-25 mg/kg, 25-30 mg/kg, 30-35 mg/kg, 35-40 mg/kg, 40-45 mg/kg, 45-50 mg/kg, 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg, 900-1000 mg/kg, 1000-1100 mg/kg, 1100-1200 mg/kg, 1200-1300 mg/kg, 1300-1400 mg/kg, 1400-1500 mg/kg, 1500-1600 mg/kg, 1600-1700 mg/kg, 1700-1800 mg/kg, 1800-1900 mg/kg, 1900-2000 mg/kg, 2000-2100 mg/kg, 2100-2200 mg/kg, 2200-2300 mg/kg, 2300-2400 mg/kg, 2400-2500 mg/kg, 2500-2600 mg/kg, 2600-2700 mg/kg, 2700-2800 mg/kg, 2800-2900 mg/kg or 2900-3000 mg/kg. In one embodiment of the invention, the ErbB4 activator is Neuregulin-4 or a pharmaceutical equivalent, analog, derivative, mimetic or a salt thereof.

Typical dosages of an effective amount of an ErbB4 activator, such as Neuregulin-4, can be in the ranges recommended by the manufacturer where known therapeutic compounds are used, and also as indicated to the skilled artisan by the in vitro responses or responses in animal models. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the effective amount of ErbB4 activator (for example, Neuregulin-4) may be administered once a day (SID/QD), twice a day (BID), three times a day (TID), four times a day (QID), or more, so as to administer an effective amount of the ErbB4 activator to the subject, where the effective amount is any one or more of the doses described herein. In various embodiments, the ErbB4 activator (such as Neuregulin-4) is administrated to the subject before, during, or after the subject develops the disease-state. In some embodiments, the composition is administrated to the subject 1-3 times per day or 1-7 times per week. In some embodiments, the composition is administrated to the subject for 1-5 days, 1-5 weeks, 1-5 months, or 1-5 years.

Pharmaceutical Compositions

In various embodiments, the present invention provides an effective amount of an ErbB4 activator, such as Neuregulin-4 or a pharmaceutical composition comprising, consisting of or consisting essentially of a therapeutically effective amount of an ErbB4 activator, such as Neuregulin-4 or a pharmaceutical equivalent, analog, derivative, mimetic or a salt thereof and a pharmaceutically acceptable excipient/carrier. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, enema, nasal, oral, sub-lingual, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of ErbB4 activator (such as Neuregulin-4) other than directly into a target site, tissue, or organ, such that it enters the subject's circulatory system and, thus, is subject to metabolism and other like processes.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. In various embodiments, the composition is administered to the subject 1-3 times per day or 1-7 times per week. In various embodiments, the composition is administered to the subject for 1-5 days, 1-5 weeks, 1-5 months, or 1-5 years. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity. While the attending physician ultimately will decide the appropriate amount and dosage regimen, therapeutically effective amounts of the ErbB4 activator as disclosed herein or a pharmaceutical equivalent, analog, derivative, mimetic or a salt thereof may be provided at a dose of 0.0001, 0.01, 0.01 0.1, 1, 5, 10, 25, 50, 100, 500, or 1,000 mg/kg or µg/kg. Effective doses may be extrapolated from dose-response curves derived from in vitro or animal model test bioassays or systems.

An effective amount as used herein would also include an amount sufficient to delay the development of a symptom of the disease, alter the course of a symptom of disease (for example but not limited to, slow the progression of a symptom of the disease), or reverse a symptom of disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent for activating ErbB4, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" or "pharmaceutically acceptable excipient" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an activator of ErbB4 (such as Neuregulin-4). Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (18) pH buffered solutions; (19) polyesters, polycarbonates and/or polyanhydrides; (20) bulking agents, such as polypeptides and amino acids (21) serum components, such as serum albumin, HDL and LDL; (22) C2-C12 alcohols, such as ethanol; and (23) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The activators of ErbB4 (such as Neuregulin-4) as described herein can be specially formulated for administration of the compound to a subject in solid, liquid or gel form, including those adapted for the following: (1) parenteral administration, for example, by subcutaneous, intramuscular, intraperitoneal, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; (7) nasally or (8) sub-lingually. Additionally, the activator of ErbB4 (such as Neuregulin-4) described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 3,270,960.

Further embodiments of the formulations and modes of administration of activator of ErbB4 (such as Neuregulin-4) that can be used in the methods described herein are illustrated below.

Parenteral Dosage Forms. Parenteral dosage forms of activator of ErbB4 (such as Neuregulin-4) can also be administered to a subject by various routes, including, but not limited to, subcutaneous, intravenous (including bolus injection), intramuscular, intraperitoneal, and intra-arterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol formulations. Activator of ErbB4 (such as Neuregulin-4) can be packaged in a pressurized aerosol container together with suitable propellants, for example, hydrocarbon propellants like propane, butane, or isobutane with conventional adjuvants. Activator of ErbB4 (such as Neuregulin-4) can also be administered in a non-pressurized form such as in a nebulizer or atomizer. Activator of ErbB4 (such as Neuregulin-4) can also be administered directly to the airways in the form of a dry powder, for example, by use of an inhaler.

Suitable powder compositions include, by way of illustration, powdered preparations of activator of ErbB4 (such as Neuregulin-4) thoroughly intermixed with lactose, or other inert powders acceptable for intra-bronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58:

1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the activator of ErbB4 (such as Neuregulin-4) described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms. In some embodiments of the methods described herein, activator of ErbB4 (such as Neuregulin-4) can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound's onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the activator of ErbB4 (such as Neuregulin-4) described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments, the activator of ErbB4 (such as Neuregulin-4) for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of the activator of ErbB4 (such as Neuregulin-4) administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Kits

The present invention is also directed to kits to treat inflammatory bowel disease, necrotizing colitis, COPD, atherosclerosis, Type I diabetes, ALI, radiation therapy-induced intestinal injury, liver fibrosis, NASH, gastroenteritis or urinary tract infections. The kit is an assemblage of materials or components, including at least one of the inventive compositions. Thus, in some embodiments the kit contains a composition including an ErbB4 activator, such as Neuregulin-4 or a pharmaceutical equivalent, analog, derivative, mimetic or a salt thereof, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat inflammatory bowel disease, necrotizing colitis, COPD, atherosclerosis, Type I diabetes, acute lung injury or liver fibrosis in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing an ErbB4 activator, such as Neuregulin-4 or a pharmaceutical equivalent, analog, derivative, mimetic or a salt thereof. The packaging material generally has an external label which indicates the contents and/or purpose of the kit and/or its components.

EXAMPLES

The following example is provided to better illustrate the claimed invention and is not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Efficient clearance of pro-inflammatory macrophages from tissue after resolution of a challenge is critical to prevent prolonged inflammation. Defects in clearance can contribute to conditions such as inflammatory bowel disease, and thus may be therapeutically targetable. However, the signaling pathways that induce termination of pro-inflammatory macrophages are incompletely defined. The inventors tested whether the ErbB4 receptor tyrosine kinase, previously not known to play a role in macrophage biology, is involved in macrophage clearance.

ErbB4 expression on macrophages and macrophage numbers in C57Bl/6 mouse colons were assessed by flow cytometry during acute DSS colitis, with or without administration of the ErbB4 ligand neureugulin-4 (NRG4). Cultured primary murine and human macrophages were activated, treated with NRG4, and apoptosis was measured. Mice deficient for ErbB4 in the myeloid lineage were subjected to DSS colitis and analyzed for colitis severity and recovery.

ErbB4 was highly expressed on pro-inflammatory macrophages during DSS colitis in mice. Pro-inflammatory activation induced ErbB4 on mouse and human macrophages in vitro. ErbB4 activation on these cells caused apoptosis dependent upon proteolytic generation of the ErbB4 intracellular domain fragment. Active inflammation suppressed NRG4 expression; this loss may allow for persistence of macrophages and ongoing inflammation. Consistent with this notion, administration of exogenous NRG4 during colitis reduced colonic macrophage numbers and improved inflammation. Furthermore, mice lacking ErbB4 in the myeloid lineage displayed worsened colitis and had impaired recovery. These data define a novel role for ErbB4 in macrophage apoptosis, and outline a mechanism of feedback inhibition that may promote resolution of colitis.

Example 1

Pro-Inflammatory Activation of Macrophages Induces ErbB4 Expression

Mø are broadly characterized along a continuum from pro-inflammatory M1 subsets involved in bacterial clearance to anti-inflammatory M2 subsets involved in homeostatic and pro-healing responses. Bone marrow-derived Mø were used for experiments in FIG. 1A-1F as these cells represent a readily expandable population of naïve monocyte/Mø that may be reliably polarized to M1 or M2 phenotype and are the source of recruited macrophages to intestinal tissue during inflammation.

To determine whether ErbB4 is regulated in Møs by pro-inflammatory activation, RNA from M1-polarized and control Møs was collected and analyzed by quantitative real-time PCR (qPCR) for all four ErbB family members expression. ErbB4 was induced 10-fold by pro-inflammatory activation (FIG. 1A; control (PBS) or IFNγ/LPS stimulated (Stim) Møs. **, $p<0.01$, n=4 mice) and was the only family member that showed an increase. Immunofluorescence analysis on Møs post-LPS also showed a marked increase in ErbB4 staining that localized to the membrane and nucleus (FIG. 1E) consistent with expression of both full-length and cleaved intracellular domain of the ErbB4 receptor (FIG. 1F).

Example 2

ErbB4 is Induced on Recruited Macrophages

C57BL/6 mice were treated with 3% dextran sodium sulfate (DSS) in water for 4 days (acute phase), followed by 3 days without DSS (inflammatory phase), or given no DSS for 7 days as a control group. Colon tissue was collected and digested using dispase II and collagenase, followed by staining for F4/80, CD11b, Ly6C, and ErbB4. Cells were processed by flow cytometry on an LSR II FACS machine and analyzed using FloJo.

Figure 2:
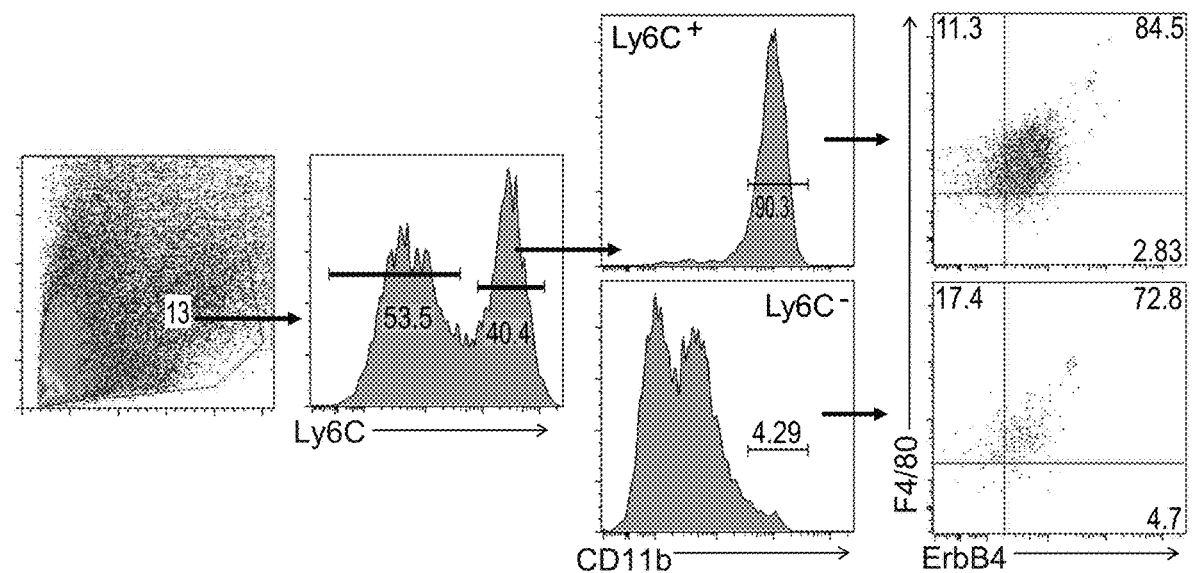
FIG. 2 depicts, in accordance with an embodiment of the invention, that ErbB4 is induced on recruited macrophages
Figure 2:
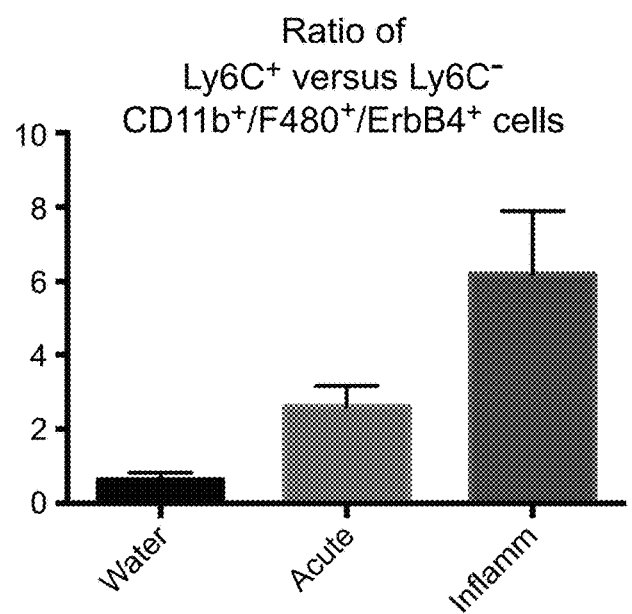

As shown in FIG. 2, there is a higher number of ErbB4+ macrophages in both inflammatory phase and acute phases following DSS induction of colitis, indicating that ErbB4+ macrophages are predominantly recruited from circulation during colitis.

Example 3

Neregulin-4 Induces Apoptosis of Pro-Inflammatory M1 Stimulated Macrophages

Figure 3A:
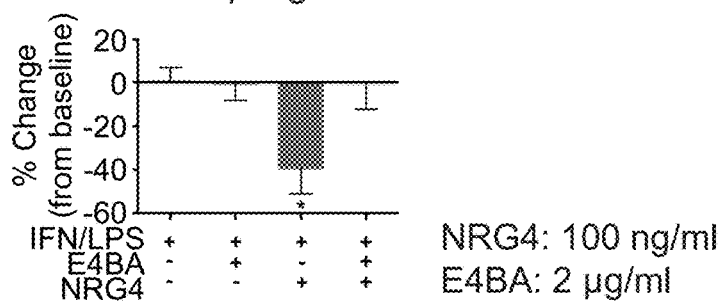
FIG. 3A-FIG. 3B depict, in accordance with an embodiment of the invention, that NRG4 induces apoptosis of M1 stimulated macrophages.

IFNγ/LPS-treated Mø were exposed to NRG4 (100 ng/ml)+/−ErbB4 blocking antibody (E4BA; 2 μg/ml) for 48 h and counted by Cell Titer Blue assay (Promega). n=4. *, $p<0.01$. As shown in FIG. 3A, ErbB4 activation reduced numbers of viable M1-polarized Mø in culture.

Figure 3B:
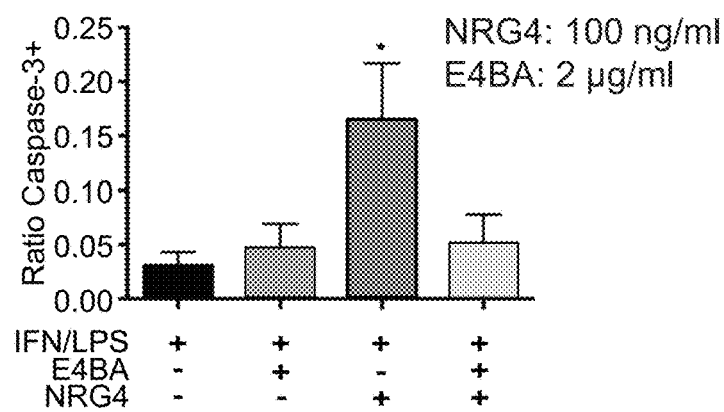
Figure 3B:
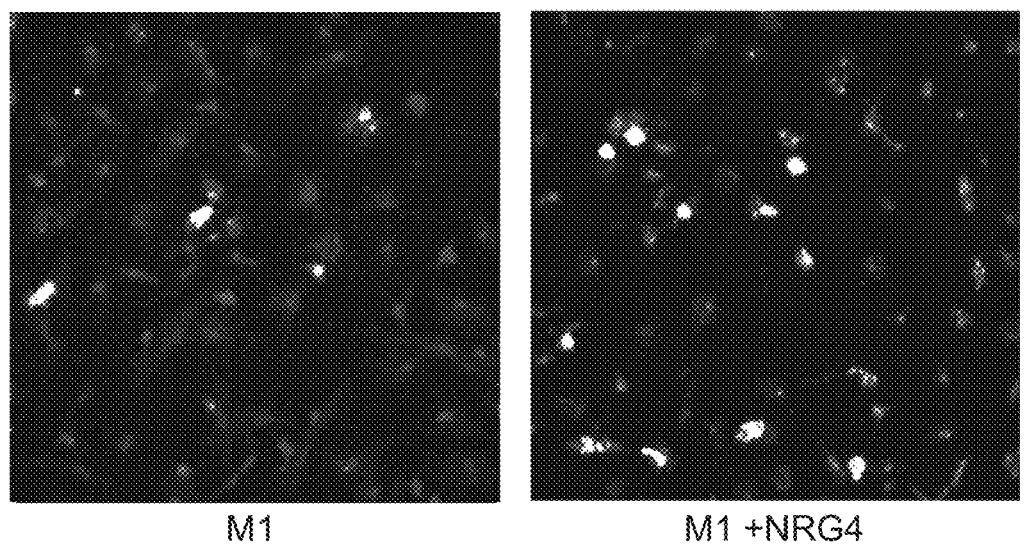

Bone-marrow derived macrophages were generated using CMG14-12 conditioned media and plated in 96-well plates. Cells were then treated with IFN-gamma overnight, followed by LPS (long/ml), with or without neuregulin-4 (NRG4) or ErbB4 neutralizing antibody (E4BA). After 48 hours cells were fixed with 4% paraformaldehyde, and stained for cleaved caspase-3 and DAPI. As shown in FIG. 3B, neuregulin-4 treatment induced a higher percentage of cells to express cleaved caspase-3, a marker of apoptosis.

Example 4

Neuregulin-4 Expression is Lost in DSS Colitis

Figure 4:
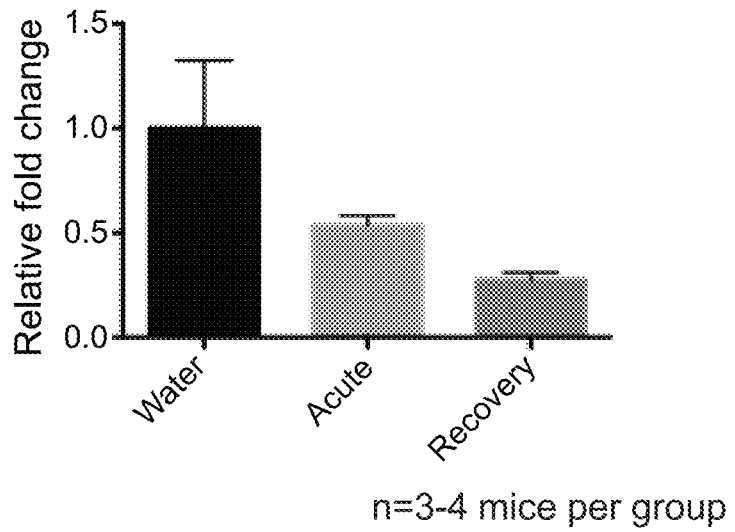
FIG. 4 depicts, in accordance with an embodiment of the invention, that NRG4 is lost in DSS colitis.

In IBD there is reduced colonic expression of the ErbB4-specific ligand NRG4, and therefore reduced capacity for NRG4-ErbB4 signaling. To determine if this is replicated in the DSS colitis model, NRG4 expression was analyzed in RNA prepared from colonic mucosal scrapings from mice treated with 3% DSS for 4 days (acute) and mice treated for 4 days with DSS plus 3 days without DSS (recovery). In comparison to untreated mice, acute and recovery DSS groups have a significant decrease in NRG4 expression (FIG. 4).

Example 5

LysM/ErbB4FF Mice have Greater Weight Loss on DSS

Mice with a deletion of ErbB4 in the myeloid cell lineage including macrophages (LysM/ErbB4$^{FF}$) and littermate controls without the deletion (ErbB4$^{FF}$) were treated with 3% DSS which was removed after 6 days. Weights were monitored daily as a measure of colitis severity.

Figure 5:
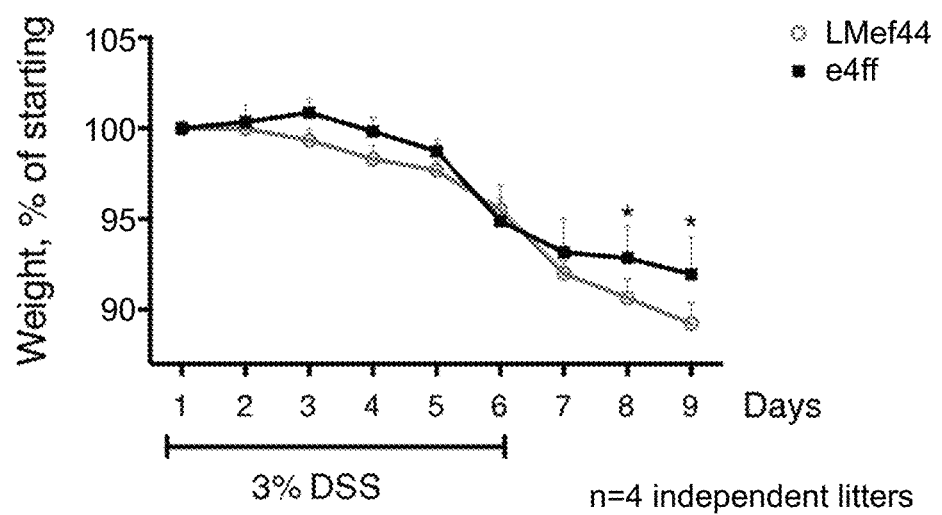
FIG. 5 depicts, in accordance with an embodiment of the invention, that LysM/ErbB4FF mice have greater weight loss on DSS.

As shown in FIG. 5, LysM/ErbB4$^{FF}$ mice lost more weight than their littermate controls indicating that loss of ErbB4 in macrophages results in a higher severity of colitis.

Example 6

NRG4 Treatment During Macrophage-Influx Ameliorates Colitis

C57BL/6 mice were treated with 3% dextran sodium sulfate (DSS) in water for 4 days followed by 3 days without DSS. Neuregulin-4 (100 µg/kg) or PBS was delivered daily by i.p. injection for the final 4 days of the experiment when macrophages are recruited to colon. Weights were monitored daily as an indicator of colitis severity. On day 7, colonic tissue was collected for flow cytometry analysis of macrophage influx and qRT-PCR analysis of macrophage-expressed inflammatory cytokines (FIG. 6A). For flow cytometry experiments, colonic tissue was digested using dispase II and collagenase, followed by staining for F4/80 and CD11b. Cells were processed by flow cytometry on an LSR II FACS machine and analyzed using FloJo. For qRT-PCR analysis, RNA was isolated from colonic tissue, converted into cDNA and analyzed for cytokine expression using TaqMan mastermix and primers.

Figure 6D:
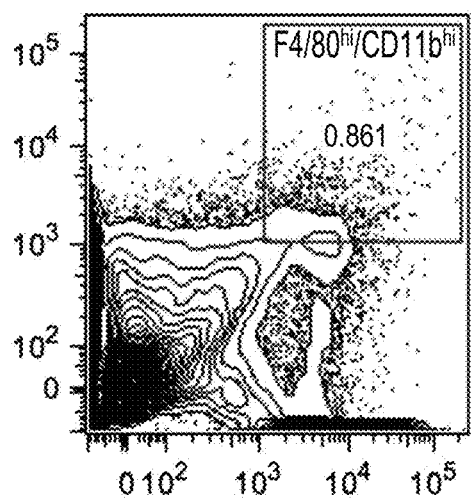
Figure 6D:
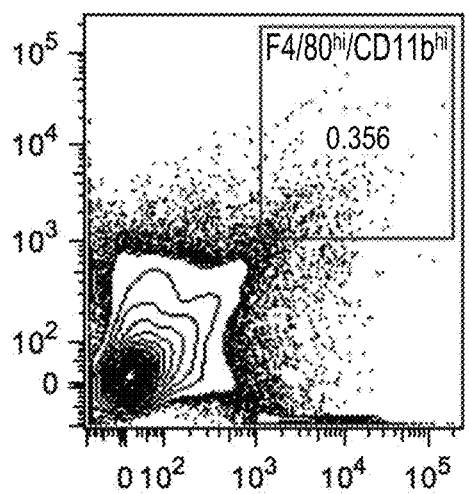
Figure 6D:
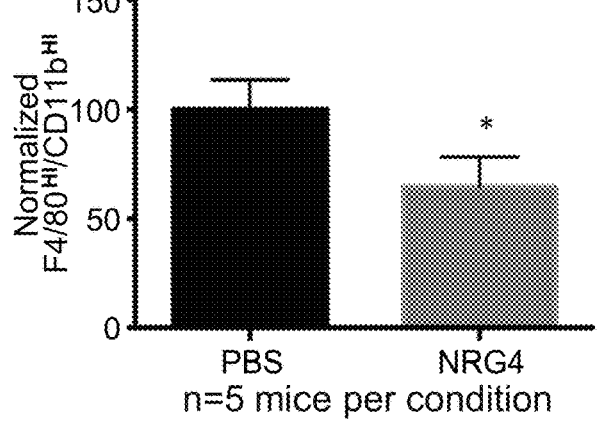

Neuregulin-4 treated mice were protected from DSS-induced weight loss (FIG. 6B) and had a lower expression of macrophage-expressed cytokines (IFN-gamma, TNF, and IL-6 (FIG. 6C)) as compared to PBS-treated mice. Analysis for F4/80+CD11b+ macrophages by flow cytometry revealed that NRG4 treatment resulted in lower macrophage numbers following DSS induced colitis (FIG. 6D).

Example 7

ErbB4-Expressing Macrophages are Present in Respiratory Inflammation

Figure 7:
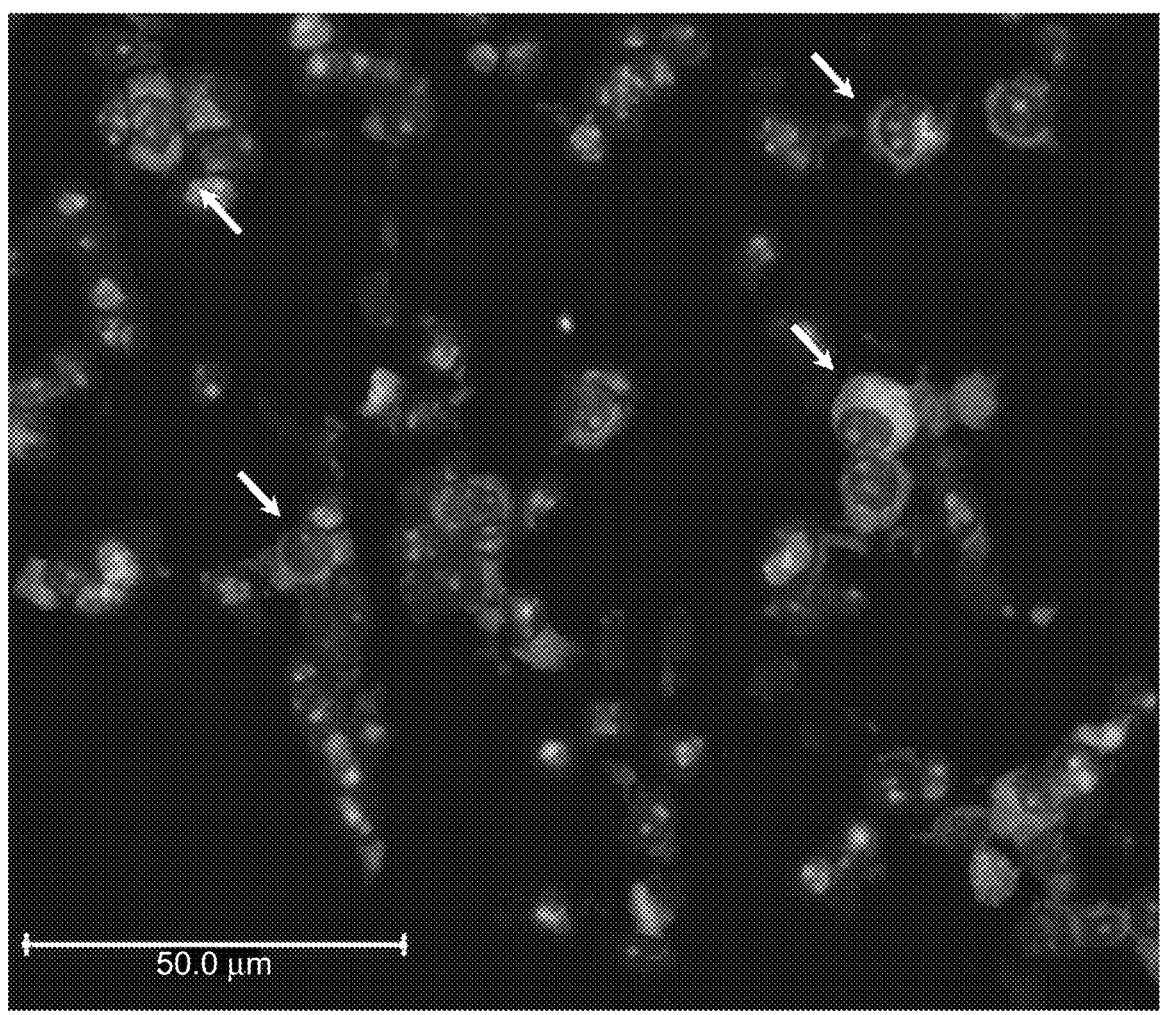
FIG. 7 depicts, in accordance with an embodiment of the invention, that ErbB4-expressing macrophages are present in respiratory inflammation.

To test whether ErbB4-expressing macrophages are also present in respiratory inflammation, sections of lungs from 8-week-old C57BL/6 mice challenged with intratracheal instillation of 50 ng/lung human recombinant annexin V 8-week-old C57BL mice by intratracheal aerosolisation, 2×weekly for 2 weeks as in Buckley et al., Eur Respir J. 2015 (PMID: 26160872). At 14 days after the last dose of annexin V (28 days after the initial instillation), lungs were fixed, paraffin embedded, and sectioned. Sections were stained for ErbB4 and F4/80 (macrophage marker). ErbB4+ macrophages (FIG. 7, examples marked by arrows in image) were readily detected in the injured lung.

Example 8

Animal Experiments:

All animal use was approved and monitored by the Children's Hospital Los Angeles Institutional Animal Care and Use Committee (Animal Welfare Assurance #A3276-01). Mice were housed under standard conditions with ad libitum water and chow access in the AAALAC-accredited animal care facility at Children's Hospital Los Angeles. C57Bl/6 mice obtained from Jackson Laboratory aged 8-12 weeks were used for experiments. For acute colitis, mice were given 3% (w/v) dextran sodium sulfate (DSS) in drinking water for 4 days (injury phase), followed by 3 days without DSS in drinking water (inflammatory phase). Stool scores were recorded on a scale of 0-4 as previously described on a continuum from fully formed pellets at 0 to liquid stool at 4 (Lin W, Ma C, Su F, Jiang Y, Lai R, Zhang T, et al. Raf kinase inhibitor protein mediates intestinal epithelial cell apoptosis and promotes IBDs in humans and mice. Gut. 2016; gutjnl-2015-310096).

Bone marrow macrophage and dendritic cell culture: Isolated bone marrow from mice was incubated with filtered CMG14-12 conditioned media (1:20) containing M-CSF to generate bone marrow-derived macrophages (BMDM) as previously described, (Takeshita S, Kaji K, Kudo A. Identification and characterization of the new osteoclast progenitor with macrophage phenotypes being able to differentiate into mature osteoclasts. J Bone Miner Res. 2000; 15(8): 1477-88; Kawane K, Fukuyama H, Yoshida H, Nagase H, Ohsawa Y, Uchiyama Y, et al. Impaired thymic development in mouse embryos deficient in apoptotic DNA degradation. Nat Immunol. 2003; 4(2):138-44; Okabe Y, Medzhitov R. Tissue-specific signals control reversible program of localization and functional polarization of macrophages. Cell. 2014; 157(4):832-44) or 20 ng/ml GM-CSF (Thermo Scientific, PMC2015) to generate bone marrow-derived dendritic cells (BMDC) as previously described (Inaba K, Inaba M, Romani N, Aya H, Deguchi M, Ikehara S, et al. Generation of large numbers of dendritic cells from mouse bone marrow cultures supplemented with granulocyte/macrophage colony-stimulating factor. JExpMed. 1992; 176:1693-702). For BMDMs, adherent cells were washed at 3 days and re-fed with M-CSF containing media until experimentation at day 7-8. For M1 polarization, cells were pre-treated with 100 U/ml IFNγ for 16 hours, then stimulated with 100 ng/ml LPS. For M2 polarization, cells were stimulated with 10 ng/ml IL-4 (Gibco, PMC0046). For BMDCs, cells were re-fed with GM-CSF at day 3 of culture. After 7 days, loosely adherent cells (enriched dendritic cell population) were transferred to new plates for experimentation. Neutrophils were isolated from bone marrow of C57/Bl7 mice by Percoll density gradient separation as previously described (Boxio R, Bossenmeyer-Pourié C, Steinckwich N, Dournon C, Nüße O. Mouse bone marrow contains large numbers of functionally competent neutrophils. J Leukoc Biol. 2004 Jan. 14; 75(4):604-11). Briefly, 100% Percoll (GE Life Sciences, 17-0891-01) (9 parts Percoll:1 part PBS) was diluted to 78%, 69%, and 52% solutions using PBS and layered in 5 ml tubes with bone marrow on the uppermost layer. After a 30 minute centrifugation at 1500 g, the layer of cells at the 78%/69% interface was isolated and used in subsequent studies.

Immunofluorescence Staining:

BMDMs grown on coverslips were fixed with ice-cold acetone for 30 minutes, blocked with 10% goat serum for 1 hour at room temperature, and incubated with 1:200 primary antibody against ErbB4 (Santa Cruz, sc-283) overnight. Antigenic peptide competition controls were performed to confirm specificity. Cells were washed and incubated with 1:1000 secondary rabbit anti-mouse Alexafluor-555 (Life Technologies) for 1 hour at room temperature following by mounting with Vectashield mounting media including DAPI (Vector Labs, H-1500).

Real-Time PCR:

RNA from cells and tissue was collected using on-column RNA isolation and purification (OMEGA Biotek), and cDNA generated with a high-capacity cDNA reverse transcriptase kit (Applied Biosystems, 4368814). Quantitative analysis of expression was performed using TaqMan assays (EGFR (Mm01187858_m1), ErbB2 (Mm00658541_m1), ErbB3 (Mm01159999_m1), ErbB4 (Mm01256793_m1), NRG4 (Mm00446254_m1), IFNγ (Mm01168134_m1), IL1β (Mm00434228_m1), TNF (Mm00443258_m1), IL6 (Mm00446190_m1), and IL12 (Mm00434169_m1), HPRT (Mm03024075_m1)) on an Applied Biosystems StepOne thermocycler. Fold change was calculated using the $2^{-\Delta\Delta Ct}$ method (Livak K J, Schmittgen T D. Analysis of relative gene expression data using real-time quantitative PCR and. Methods. 2001; 25(4):402-8). Results are expressed as average fold change in gene expression relative to control or non-treatment group using HPRT as the reference gene.

Western Blotting:

Protein lysates from cells and tissue were collected and lysed in RIPA buffer (Frey M R, Edelblum K L, Mullane M T, Liang D, Polk D B. The ErbB4 Growth Factor Receptor Is Required for Colon Epithelial Cell Survival in the Presence of TNF. Gastroenterology. 2009; 136(1):217-26) with Halt Protease inhibitor cocktail (Thermo Scientific, #1861278), and phosphatase inhibitor cocktails 2 and 3 (Sigma, P5726 and P0044). Protein concentration was determined by DC protein assay (Bio-Rad, #500). 30 µg protein/condition were separated by SDS-PAGE (Thermo Scientific, NW0412A) and transferred to nitrocellulose membrane. Membranes were blocked with 5% milk and probed with 1:1000 EGFR (Cell Signaling #4267), 1:1000 ErbB2 (Cell Signaling #2165), 1:1000 ErbB3 (Cell Signaling #12708), 1:1000 rabbit anti-ErbB4 (Santa Cruz, sc-283) overnight at 4° C. or 1:10,000 mouse anti-Actin (Sigma, A1978) for 1 hour at room temperature, followed by 1:10,000 IRDye-conjugated donkey anti-rabbit (LI-COR, #926-68023) and donkey anti-mouse (LI-COR, #926-32212) for 1 hour at room temperature and quantification on an Odyssey imager (LI-COR).

Murine Cell Viability and Apoptosis Assays:

BMDMs were plated in 96 well plates at 40,000 cells per well. Cells were washed and plated in DMEM with 10% heat-inactivated FBS, 100 U/ml penicillin and streptomycin, and given 100 U/ml IFNγ overnight. In some experiments cells were then pre-treated for 30 minutes with 2 µg/ml ErbB4 neutralizing antibody (Millipore, 05-478) (Jay S M, Kurtagic E, Alvarez L M, De Picciotto S, Sanchez E, Hawkins J F, et al. Engineered bivalent ligands to bias ErbB receptor-mediated signaling and phenotypes. J Biol Chem. 2011; 286(31):27729-40) before incubation with 100 ng/ml NRG4 (Reprokine) for 1 hour then LPS (100 ng/ml) for 48 hours. Some cells were pre-treated with the metalloprotease inhibitor GM6001 (Tocris, #2983) at 10 µM, γ-secretase inhibitor DAPT (Tocris, #2634) at 10 µM, or ADAM17 inhibitor, GW280264X at 3 µM (Aobious, Inc.) prior to NRG4 and LPS treatment as described in Results. Relative cell numbers were determined by Cell Titer Blue (resazurin-based assay) following manufacturer's instructions (Promega, G8081). For active caspase-3 analysis in BMDMs, cells were fixed with ice cold acetone for 30 minutes and incubated overnight at 4° C. with antibody against cleaved caspase-3 pre-conjugated to Alexa Fluor 488 (Cell Signaling, #9669). The following day, cells were washed 5× with PBS for 5 minutes each and imaged. For a cumulative view of apoptosis events, we performed analysis of membrane phosphatidylserine flip with annexin V staining. Following treatment, cells were stained with annexin V and propidium iodide using the annexin V apoptosis kit (Life Technologies, V13241) and analyzed on an LSR II flow cytometer (BD Biosciences).

Primary Human Myeloid Cell Culture, MDM Polarization, and Cell Survival:

Informed consent was obtained per protocol approved and monitored by the institutional review board at Yale University. We recruited healthy individuals with no personal or family history of autoimmune/inflammatory disease, including psoriasis, SLE, rheumatoid arthritis, multiple sclerosis, type I diabetes mellitus, Crohn's disease, and ulcerative colitis, or a history of HIV. Human peripheral blood mononuclear cells (PBMCs) were isolated using Ficoll-Paque (GE Dharmacon). Monocytes were purified from PBMCs by positive CD14 selection (Miltenyi Biotec) or adhesion, tested for purity, and cultured with M-CSF (long/ml) (Shenandoah Technology) for 7 days for MDM differentiation in the presence of 10% fetal bovine serum (Sigma-Aldrich). MDMs were stimulated with 100 ng/ml LPS (Sigma-Aldrich) and 20 ng/ml IFN-γ (R&D Systems) (M1 polarization) or 20 ng/ml IL-4 (R&D Systems) (M2 polarization), with or without NRG4. Where indicated, cultures were transfected with 100 nM scrambled or ON-TARGETplus SMARTpool siRNAs (a pool of four distinct, commercially designed siRNA) against ErbB4 (GE Dharmacon) using Amaxa nucleofector technology (Amaxa, San Diego, Calif.). Apoptosis was detected by flow cytometry with annexin V (eBiosciences). Intracellular proteins were detected in permeabilized cells by flow cytometry with anti-ErbB4 (Abcam, ab32375).

Flow Cytometry:

To generate a single cell suspension, colonic mucosa was isolated and digested for 30 minutes at 37 C in 100 ml DMEM with 2% heat-inactivated FBS, 0.2 mg/ml dispase II (Sigma, D4693), 2 mg/ml collagenase D (Roche, #11088882001), and 0.2 mg/ml DNase I (Sigma, DN25) as previously described (Punit S, Dube P E, Liu C Y, Girish N, Washington M K, Polk D B. Tumor Necrosis Factor Receptor 2 Restricts the Pathogenicity of CD8+ T Cells in Mice with Colitis. Gastroenterology. 2015; 149(4):993-1005.e2). For population analysis experiments, cells were fixed with 4% formaldehyde followed by permeabilization with 0.01% saponin. Cells were incubated with FcBlock (BD Biosciences, 553142, 1:100) for 15 minutes in FACS buffer (PBS+1% heat-inactivated FBS), followed by incubation for 30 minutes with the following fluorophore pre-conjugated antibodies: F4/80-Alexafluor 488 (Life Technologies, MF48020, 1:100), CD11b-APC (Life Technologies, RM2805, 1:100), and Ly6C-BV421 (BD Biosciences, 562727, 1:100). Cells were also incubated with primary antibody against monoclonal ErbB4 (Abcam, ab32375, 1:40) for 30 minutes followed by anti-rabbit PE (Abcam, A10542, 1:100) for 30 minutes. Cells were analyzed on an LSR II flow cytometer (BD Biosciences).

Statistical Methods:

Statistical analyses and plots were generated using Prism (GraphPad Software). Mean+/−SEM is depicted in bar graphs. Student's t test or ANOVA with Tukey post-hoc test to correct for multiple comparisons were used to determine statistical differences, as appropriate. Statistical significance was assigned top <0.05.

Classical Activation of Macrophages Induces, while Alternative Activation Inhibits, ErbB4 Expression The ErbB receptor tyrosine kinases have been predominantly investigated for their roles in epithelial cell growth and migration. However, recent studies demonstrated that some members of this family are also present on immune cells, including macrophages (Tynyakov-Samra E, Auriel E, Levy-Amir Y, Karni A. Reduced ErbB4 Expression in Immune Cells of Patients with Relapsing Remitting Multiple Sclerosis. Mult Scler Int. 2011; 2011:561262; Lu N, Wang L, Cao H, Liu L, Van L, Washington M K, et al. Activation of the Epidermal Growth Factor Receptor in Macrophages Regulates Cytokine Production and Experimental Colitis. J Immunol. 2015; 192(3):1013-23). We have previously shown that ErbB4, the most biochemically distinct member of this receptor family, is induced in inflamed tissue (Bernard J K, McCann S P, Bhardwaj V, Washington M K, Frey M R. Neuregulin-4 is a survival factor for colon epithelial cells both in culture and in vivo. J Biol Chem. 2012 Nov. 16; 287(47):39850-8), but whether it has a role in macrophages has not been addressed.

Figure 1B:
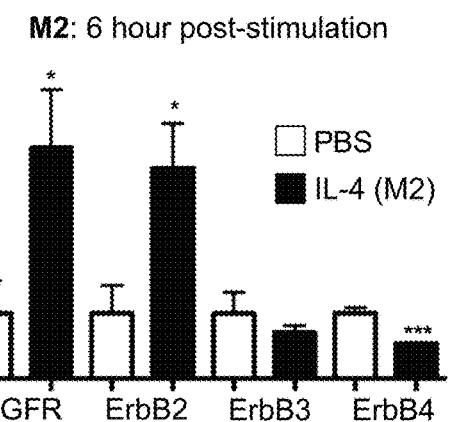

Macrophages exist along a continuum of sub-types that perform a variety of pro- and anti-inflammatory functions, as well as tissue repair. To experimentally assess their function in vitro, macrophages can be driven toward a pro-inflammatory state (classical M1 activation) involved in bacterial clearance, or an anti-inflammatory state (alternative M2 activation) involved in homeostatic and pro-healing responses (Mosser D M, Edwards J P. Exploring the full spectrum of macrophage activation. Nat Rev Immunol. 2008; 8(12):958-69). We generated and polarized bone marrow-derived macrophages (BMDM) to M1 and M2 states, and determined the expression pattern of ErbB family members by qPCR. Classical activation with interferon (IFN) γ+lipopolysaccharide (LPS) induced ErbB4 10-fold after 6 hours, while in contrast the other ErbB family members EGFR, ErbB2, and ErbB3 were all significantly decreased (FIG. 1A). We also observed induction of ErbB4 mRNA in the immortalized macrophage cell line, RAW267.01, following pro-inflammatory activation with IFNγ+LPS (data not shown). To test if this response was specific to pro-inflammatory M1 activation, we also examined macrophages alternatively polarized to an M2 state with interleukin (IL)-4. M2 polarization did not induce ErbB4, but instead resulted in a significant decrease in its expression (FIG. 1B). These data suggest that, among macrophage populations, ErbB4 is largely restricted to pro-inflammatory cells.

Figure 1C:
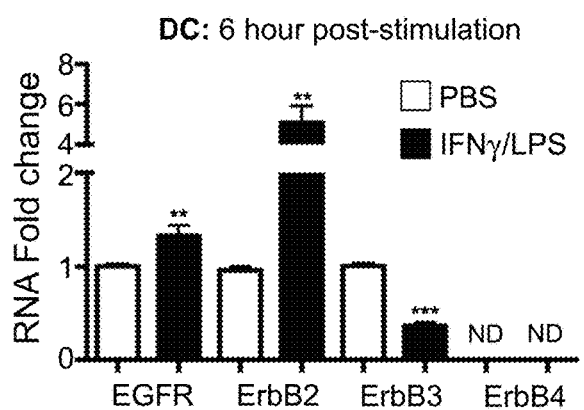
Figure 1D:
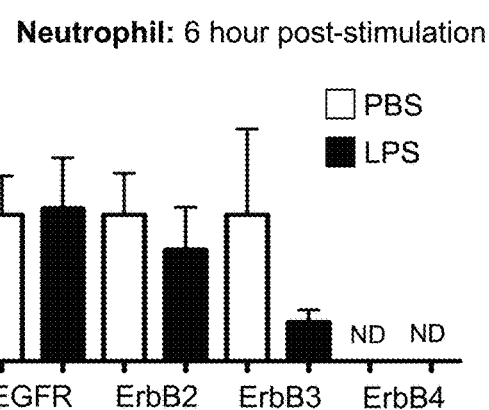

As other innate immune cells (dendritic cells, and neutrophils) can also respond to bacterial cell membrane LPS (Ling G S, Bennett J, Woollard K J, Szajna M, Fossati-Jimack L, Taylor P R, et al. Integrin CD11b positively regulates TLR4-induced signalling pathways in dendritic cells but not in macrophages. Nat Commun. 2014; 5:3039-51), we tested whether induction of ErbB4 is a general feature of TLR4-induced signaling in innate myeloid cells by exposing bone-marrow derived dendritic cells (BMDCs) to IFNγ+LPS or bone-marrow isolated neutrophils to LPS. BMDCs stimulated with LPS displayed a distinct profile of ErbB regulation, and ErbB4 was not detectable in these cells (FIG. 1C). Furthermore, bone-marrow isolated neutrophils stimulated with LPS also had undetectable levels of ErbB4 (FIG. 1D). This suggests that ErbB4 induction by LPS is a macrophage-specific outcome, rather than a generic TLR4 response.

To confirm ErbB4 induction in M1 macrophages at the protein level, we performed immunofluorescence and western blot analysis. Immunofluorescence staining on LPS-challenged macrophages demonstrated elevated ErbB4 protein expression, both at the plasma membrane and within the cell (FIG. 1E). This pattern is consistent with the expression of both full-length and proteolytically cleaved intracellular domain (4ICD) forms of the receptor (Williams C C, Allison J G, Vidal G A, Burow M E, Beckman B S, Marrero L, et al. The ERBB4/HER4 receptor tyrosine kinase regulates gene expression by functioning as a STAT5A nuclear chaperone. J Cell Biol. 2004; 167(3):469-78). ErbB4 protein induction (both full-length and 4ICD) was also observed by western blot analysis of naïve versus M1 macrophages (FIG. 1F) and LPS-treated RAW267.01 cells.

The ErbB4-Specific Ligand NRG4 Induces Pro-Inflammatory Macrophage Apoptosis

To determine the role of ErbB4 in pro-inflammatory macrophage biology, we stimulated signaling in these cells using an ErbB4-specific ligand expressed in intestinal tissue, NRG4. Following 48 hours treatment, we observed a significant decrease in cell numbers in M1 but not M2 macrophages, indicating that NRG4 selectively inhibits M1 macrophage growth or survival (FIG. 8A). LPS activation of macrophages has been reported to halt cell proliferation; we confirmed this in our cultures with EdU staining, and furthermore saw no change in % EdU uptake with or without NRG4, ruling out effects on proliferation. Therefore, we asked whether ErbB4 activation was inducing cell death. NRG4 exposure caused a significant increase in cleaved caspase-3 staining (FIG. 8B), indicative of ongoing late-stage apoptosis of these cells. This response was blocked by pre-treatment with ErbB4 neutralizing antibody, demonstrating a requirement for NRG4-ErbB4 binding. As another measure of apoptosis that assesses cumulative apoptosis events over time, we performed annexin V analysis. Similar to the cleaved caspase-3 results, annexin V staining revealed a significant increase in apoptosis in response to NRG4 treatment (FIG. 8C). These results suggest stimulation of ErbB4 signaling in pro-inflammatory macrophages is a mechanism that limits accumulation of these cells.

NRG4-Induced Macrophage Death Requires Protease Activity

Figure 9A:
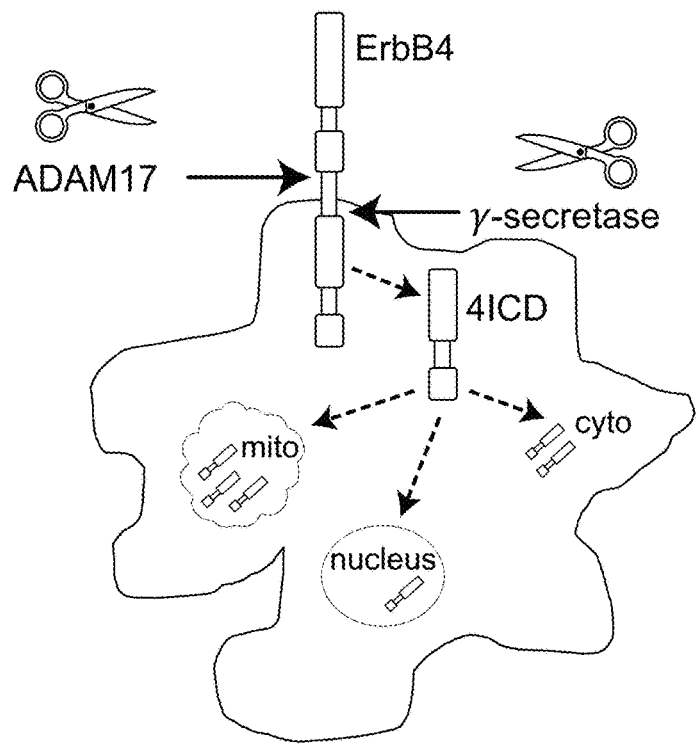
Figure 9B:
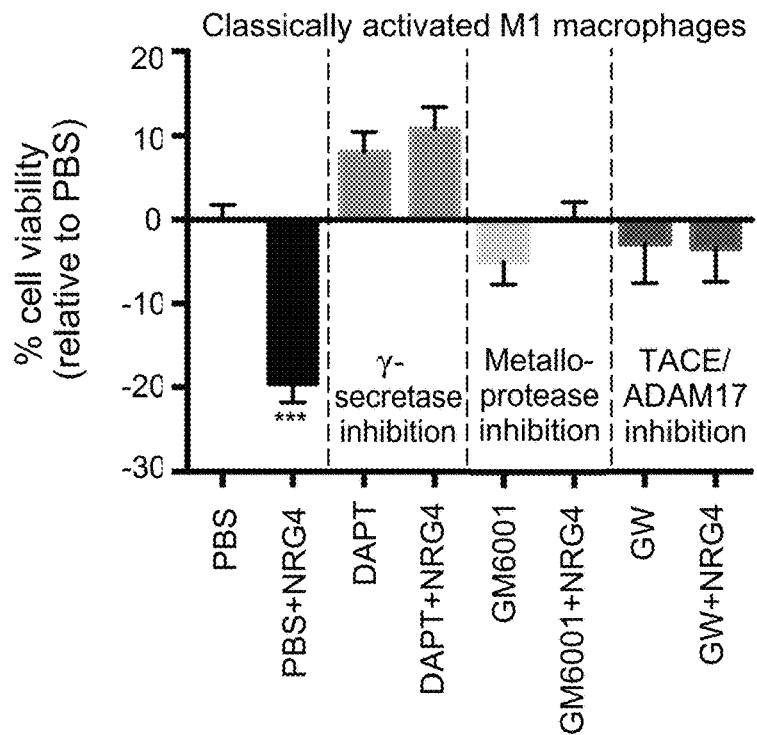

Ligand-driven two-step proteolytic cleavage of ErbB4 (by TACE/ADAM17 followed by γ-secretase) occurs in some cell types; the resulting soluble 4ICD intracellular domain fragment can localize to the cytoplasm, nucleus, or mitochondria to regulate cellular behavior (FIG. 9A). Notably, in breast cancer cells, 4ICD association with mitochondria stimulates apoptosis (Naresh A, Long W, Vidal G A, Wimley W C, Marrero L, Sartor C I, et al. The ERBB4/HER4 intracellular domain 4ICD is a BH3-only protein promoting apoptosis of breast cancer cells. Cancer Res. 2006; 66(12): 6412-20), though this has not been observed in non-transformed cells. We used protease inhibitors to test whether this mechanism might play a role in NRG4-induced macrophage apoptosis. Inhibition of either γ-secretase (DAPT, 10 μM), broad metalloprotease activity (GM6001, 10 μM), or TACE/ADAM17 (GW280264X, 3 μM) protected against the NRG4-induced cell death (FIG. 9B). Consistent with this observation, ErbB4 co-localized with mitochondria in macrophages after NRG4 treatment (FIG. 9C), suggesting the effects of NRG4 may be through 4ICD generation and possibly stimulation of the mitochondrial apoptosis pathway.

Figure 10A:
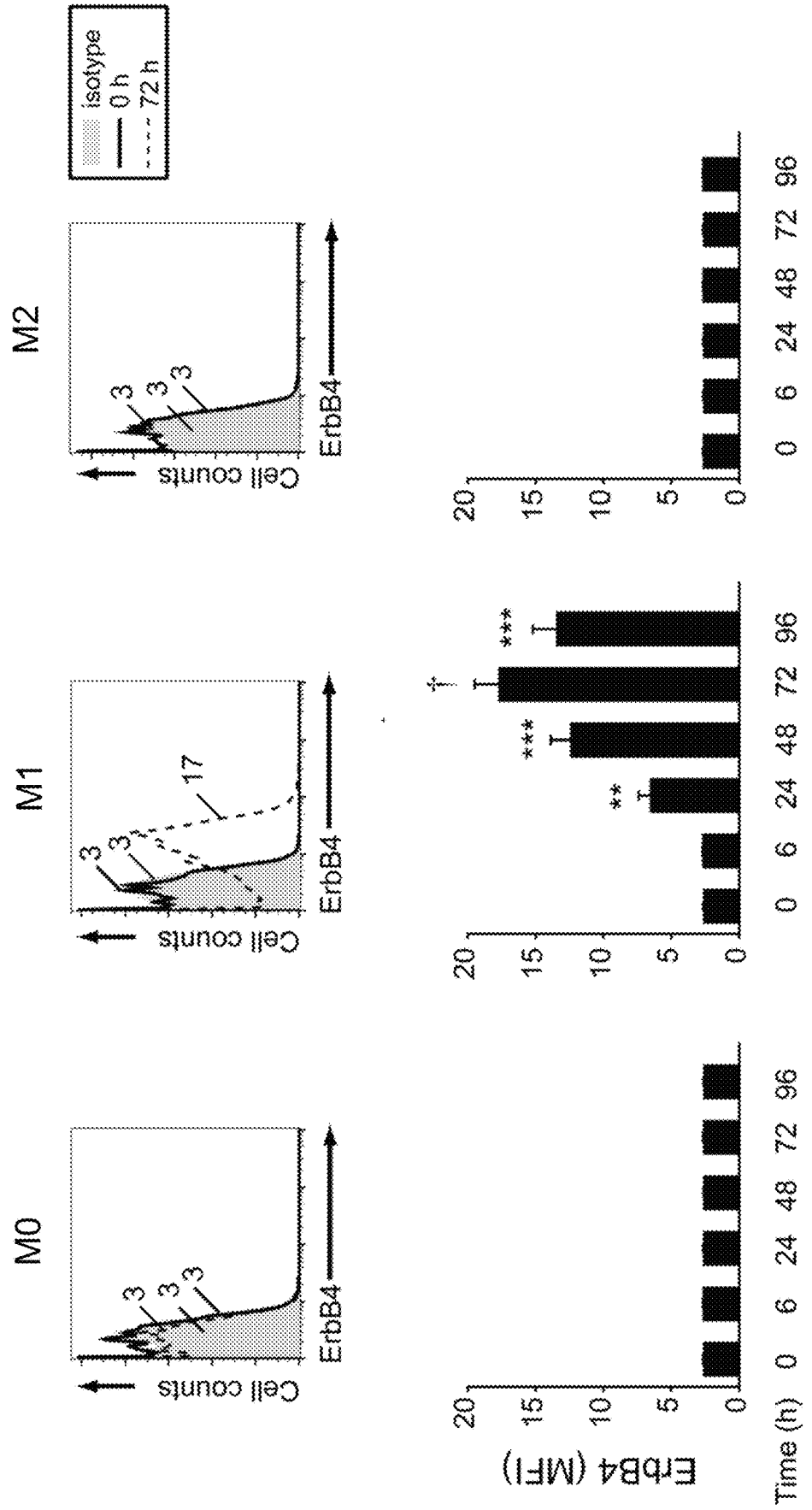
FIG. 10A-FIG. 10C depict, in accordance with an embodiment of the invention, that ErbB4 is induced on human monocyte-derived macrophages by pro-inflammatory activation, and mediates NRG4-induced apoptosis.
Figure 10B:
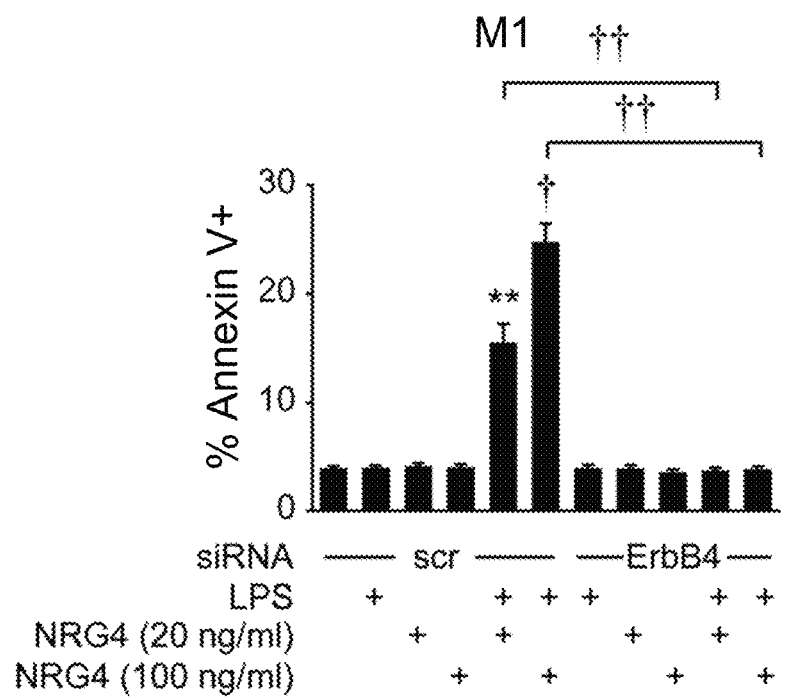
Figure 10C:
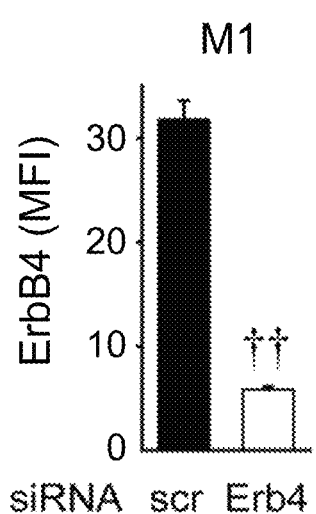

Classically Activated Human Macrophages Express ErbB4 and Undergo Apoptosis in Response to NRG4 Stimulation To assess the relevance of our findings to human biology, we generated and polarized macrophages from peripheral blood mononuclear cells (PBMCs) and assessed ErbB4 expression by flow cytometry. Similar to murine cells, pro-inflammatory M1 activation of human macrophages induced ErbB4 expression, assessed here by flow cytometry for protein expression (FIG. 10A). Induction was sustained at least 96 hours post-stimulation, suggesting capacity to respond to ligand is maintained over time. Alternative M2 activation of these cells had no effect on ErbB4 levels (FIG. 10A). Similar to our findings in the mouse, NRG4 exposure elicited a dose-dependent apoptosis of human M1 macrophages as measured by annexin V staining (FIG. 10B). Effective ErbB4 knockdown with siRNA (FIG. 10C) abrogated this response (FIG. 10B), confirming receptor specificity. Our findings suggest a conserved role for the ErbB4 signaling axis in macrophage biology between species, and underscore the potential relevance of this feedback mechanism in maintenance of human health.

Figure 11A:
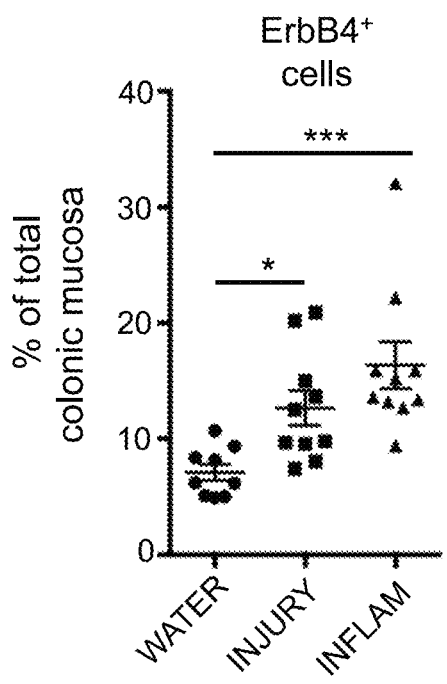
FIG. 11A-FIG. 11C depict, in accordance with an embodiment of the invention, that ErbB4 is induced during DSS colitis and is expressed on Ly6C+ macrophages.
Figure 11B:
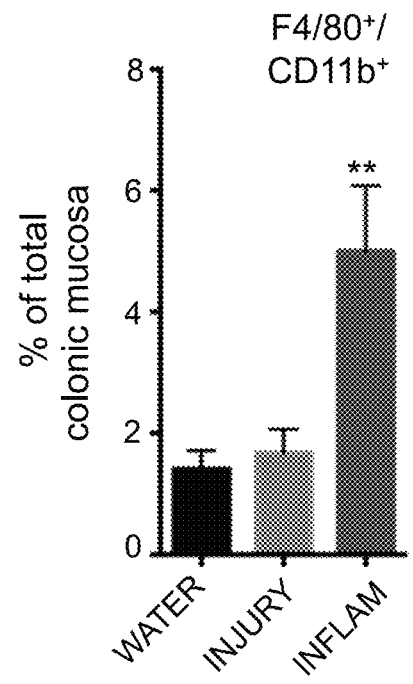
Figure 11C:
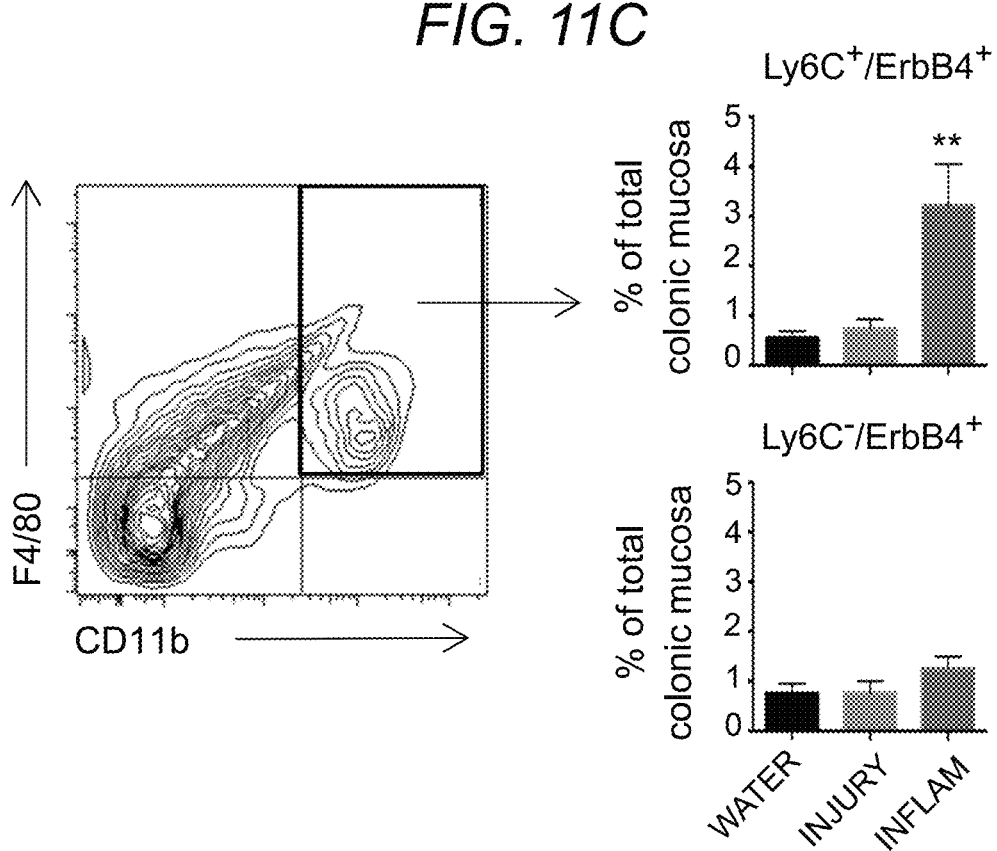

ErbB4 is Induced During DSS Colitis and Expressed on Ly6C$^+$ Inflammatory Macrophages To determine if macrophage-expressed ErbB4 plays a role in intestinal inflammatory disease in vivo, we tested whether ErbB4 is expressed on recruited macrophages in the dextran sodium sulfate (DSS) experimental model of murine colitis. In this model, Ly6C$^+$ inflammatory macrophage influx is critical for pathogenesis (Axelsson L G, Landström E, Goldschmidt T J, Gronberg A, Bylund-Fellenius A C. Dextran sulfate sodium (DSS) induced experimental colitis in immunodeficient mice: effects in CD4(+)-cell depleted, athymic and NK-cell depleted SCID mice. Inflamm Res. 1996; 45(4):181-91; Zigmond E, Varol C, Farache J, Elmaliah E, Satpathy A T, Friedlander G, et al. Ly6Chi monocytes in the inflamed colon give rise to proinflammatory effector cells and migratory antigen-presenting cells. Immunity. 2012; 37(6):1076-90). Mice were given 3% (w/v) DSS in drinking water for 4 days to elicit acute colonic damage (injury phase), followed by 3 days without DSS (inflammatory phase). Consistent with our previously published findings (Frey M R, Edelblum K L, Mullane M T, Liang D, Polk D B. The ErbB4 Growth Factor Receptor Is Required for Colon Epithelial Cell Survival in the Presence of TNF. Gastroenterology. 2009; 136(1):217-26), we confirmed an overall increase in ErbB4$^+$ cells in the colon by flow cytometric analysis of single-cell dissociated mucosa (FIG. 11A). Also as expected, numbers of F4/80$^+$/CD11b$^+$ macrophages in the colon were significantly increased by the inflammatory phase at day 7 (FIG. 11B). To characterize ErbB4 expression on these cells, we analyzed the F4/80$^+$/CD11b$^+$ population for ErbB4 as well as Ly6C, which marks inflammatory monocytes/macrophages recruited to tissue during inflammation. By the inflammatory phase, a novel population of Ly6C/ErbB4$^+$ macrophages emerged in the colons (FIG. 11C). The majority of ErbB4$^+$ macrophages were Ly6C$^+$, as the Ly6C$^-$/ErbB4$^+$ population was not significantly altered. Together these results demonstrate that ErbB4 is expressed on inflammatory Ly6C$^+$ macrophages recruited to the colon during inflammation.

Figure 12D:
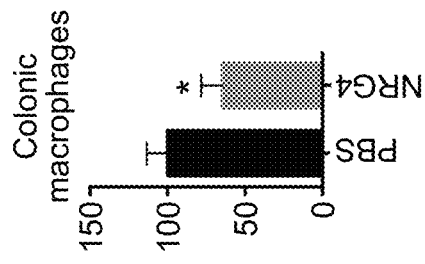
(FIG. 12D) Weights were recorded daily for mice given 3% DSS in drinking water for 4 days, then removed from DSS and given daily i.p. injections of NRG4 (100 µg/kg).

NRG4 is Repressed by DSS Colitis and Re-Administration Reduces Macrophage Load in the Inflamed Colon We have previously shown that in human IBD and chronic mouse colitis, expression of the ErbB4-specific ligand NRG4 is lost, potentially leading to a dysregulated ErbB4 signaling axis (Bernard J K, McCann S P, Bhardwaj V, Washington M K, Frey M R. Neuregulin-4 is a survival factor for colon epithelial cells both in culture and in vivo. J Biol Chem. 2012 Nov. 16; 287(47):39850-8). NRG4 is most prominently expressed in the mesenchyme of the colon (Bernard J K, McCann S P, Bhardwaj V, Washington M K, Frey M R. Neuregulin-4 is a survival factor for colon epithelial cells both in culture and in vivo. J Biol Chem. 2012 Nov. 16; 287(47):39850-8), though Feng and Teitelbaum have also detected expression in epithelium (Feng Y, Tsai Y, Xiao W, Ralls M W, Stoeck A, Wilson C L, et al. Loss of ADAM17-Mediated Tumor Necrosis Factor Alpha Signaling in Intestinal Cells Attenuates Mucosal Atrophy in a Mouse Model of Parenteral Nutrition. Mol Cell Biol. 2015; 35(21):3604-21) and we have detected regulated expression in enteroids and immune cells. Thus, NRG4 is likely sourced from multiple cell types in the colon. To determine if loss of NRG4 in colitis is driven by acute processes early in the injury/inflammation cycle, we analyzed colonic tissue from mice after 4 days of 3% (w/v) DSS exposure (injury phase) and 3 days post-DSS (inflammatory phase). NRG4 expression was reduced at the injury phase with further down-regulation observed during the inflammatory phase, indicating that NRG4 repression occurs early in colitis and is maintained throughout recruitment of inflammatory macrophages (FIG. 12A). As expected, increases in tissue and macrophage-derived pro-inflammatory cytokines TNF, IFNγ, IL1β, and IL-12 were observed following DSS treatment (FIG. 12A). Previous reports have suggested that pro-inflammatory cytokines may inhibit NRG4 expression in adipocytes (Wang G X, Zhao X Y, Meng Z X, Kern M, Dietrich A, Chen Z, et al. The brown fat-enriched secreted factor Nrg4 preserves metabolic homeostasis through attenuation of hepatic lipogenesis. Nat Med. 2014 Nov. 17; 20(12):1436-43) or the intestine (Feng Y, Tsai Y, Xiao W, Ralls M W, Stoeck A, Wilson C L, et al. Loss of ADAM17-Mediated Tumor Necrosis Factor Alpha Signaling in Intestinal Cells Attenuates Mucosal Atrophy in a Mouse Model of Parenteral Nutrition. Mol Cell Biol. 2015; 35(21):3604-21; Feng Y, Teitelbaum D H. Epidermal growth factor/TNF-α transactivation modulates epithelial cell proliferation and apoptosis in a mouse model of parenteral nutrition. Am J Physiol Gastrointest Liver Physiol. 2012; 302(2):G236-49). Consistent with these observations, there was a significant negative correlation (r=−0.421; p=0.02) between TNF and NRG4 (FIG. 12B, 12C). These observations extend our previous work showing that NRG4 is lost in IBD by showing this inhibition occurs acutely during the initiation of colonic inflammation. Furthermore, these findings suggest NRG4 expression may be suppressed either directly by TNF, or by the same pathogenic processes that induce TNF.

Figure 12E:
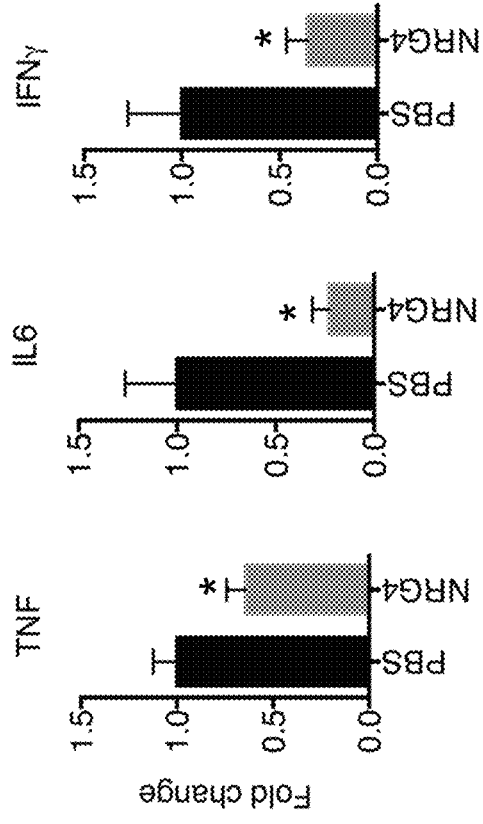
(FIG. 12E) At day 7, colonic homogenates were analyzed for macrophage-associated pro-inflammatory cytokine levels by qPCR.
Figure 12F:
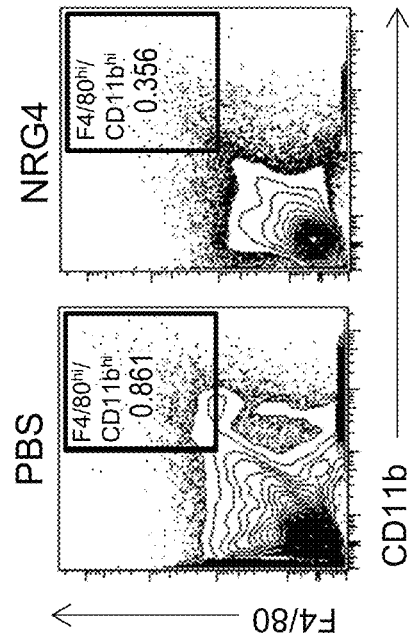
(FIG. 12F) Colitis parameters were measured at day 7 and (FIG. 12G) colonic single cell suspensions were analyzed by flow cytometry for F4/80HI/CD11bHI macrophage levels, and quantified (FIG. 1211). n=10 mice per group. Error bars represent SEM. *, $p<0.05$; , $p<0.01$; *, $p<0.001$; †, $p<1\times10-4$.
Figure 12G:
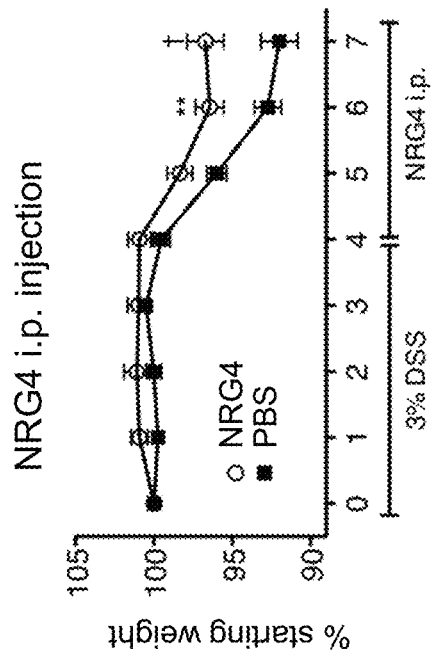
Figure 12H:
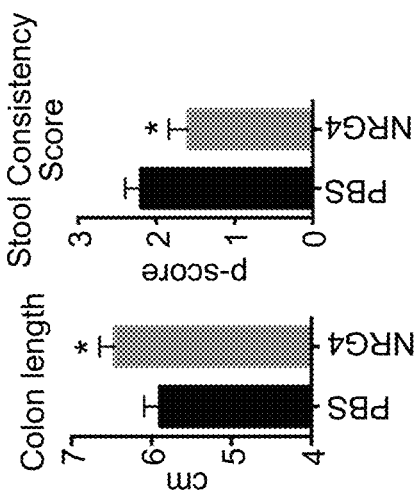

To test if replacing NRG4 during colitis therapeutically alters the macrophage population, mice were given DSS to establish colitis, and then were treated with daily intraperitoneal injections of NRG4 (100 µg/kg) between days 4 and 7, the period of maximal macrophage influx (FIG. 11B). NRG4 treatment reversed DSS-induced weight loss (FIG. 12D), reduced levels of the macrophage-expressed pro-inflammatory cytokines TNF, IL6, and IFNγ (FIG. 12E), and ameliorated colon shortening and diarrhea (FIG. 12F). Flow cytometric analysis of colonic single cell suspensions for F4/80'/CD11b' cells showed that, consistent with our in vitro observations, NRG4 treatment resulted in a 36% decrease in macrophage numbers in colonic tissue (FIG. 12G, 12H). Thus, when given therapeutically in established acute colitis, NRG4 reduces macrophage numbers in the colon and ameliorates disease.

Dysregulated inflammation is an underlying feature of many chronic diseases, including IBD. In the intestinal tract, where transient damage and interaction with foreign microbes are frequent, tissue inflammation must initiate rapidly and aggressively to effectively clear a challenge, but must also resolve efficiently to prevent host damage and chronicity. Therefore, anti-inflammatory feedback mechanisms must readily terminate pro-inflammatory responses to maintain homeostasis. Herein the inventor reports the novel finding that ErbB4 signaling provides an example of such a mechanism. This is one of the few known tissue-derived signals promoting resolution of colonic inflammation through pro-inflammatory macrophage death.

Macrophages are crucial mediators of inflammation in the gut. Pro-inflammatory $Ly6C^+$ macrophages orchestrate recruitment and activation of adaptive immune responses and aggressively secrete inflammatory factors (TNF, IFNγ, IL-1β, IL-12) that can result in epithelial damage and loss of barrier function. Therefore, tight control of these cells is necessary to prevent aberrant or chronic inflammation. In animal models, $Ly6C^+$ macrophages recruited from the bloodstream potentiate inflammation, suggesting that overactive responses may contribute to disease. In contrast, tissue resident macrophage populations ($CX_3CR_1^+$) integrate and secrete anti-inflammatory signals to prevent colitis and promote tissue repair and resolution. Identifying subset-specific regulatory mechanisms in macrophage populations is a crucial step towards harnessing these populations therapeutically. Our results show that ErbB4 is a key signaling pathway that limits cell survival specifically in $Ly6C^+$ pro-inflammatory, but not in naïve or anti-inflammatory, macrophages (FIG. 8A-8C).

The data shows that pro-inflammatory activation of macrophages induces robust ErbB4 receptor expression, and acute colitis is associated with recruitment of ErbB4-expressing macrophages (FIG. 1A-1F and FIG. 11A-11C). In recent years, an increasing number of reports have shown that growth factor receptors, such as the EGFR/ErbB family, FGFRs, and IGF-R, traditionally implicated in regulating epithelial cell function, are also expressed in hematopoietic cell lineages. To date, however, little is known about what regulates their expression or what role ErbB receptors play in immune cells. Growth factor signals may perform very different functions in immune cells versus their established pro-growth and survival functions in epithelium. However, macrophage sub-type expression, a functional role for ErbB4 in macrophage biology, and the expression of ErbB4 in colonic macrophages had not been identified to date.

The finding that ErbB4 signaling in macrophages leads to cell death might seem unexpected in that previous studies with non-transformed cells have largely observed a pro-survival role (Määttä JA, Sundvall M, Junttila T T, Peri L, Laine V J O, Isola J, et al. Proteolytic cleavage and phosphorylation of a tumor-associated ErbB4 isoform promote ligand-independent survival and cancer cell growth. Mol Biol Cell. 2006; 17(1):67-79; Kang H G, Jenabi J M, Zhang J, Keshelava N, Shimada H, May W A, et al. E-cadherin cell-cell adhesion in Ewing tumor cells mediates suppression of anoikis through activation of the ErbB4 tyrosine kinase. Cancer Res. 2007; 67(7):3094-105; Bernard J K, McCann S P, Bhardwaj V, Washington M K, Frey M R. Neuregulin-4 is a survival factor for colon epithelial cells both in culture and in vivo. J Biol Chem. 2012 Nov. 16; 287(47):39850-8). However, an apoptotic response to ErbB4 in breast cancer cells has been previously observed, and our findings in macrophages may involve a similar mechanism. In both macrophages (FIG. 9A-9C) and breast cancer cells, proteolytic activity appears to be necessary for neuregulin-stimulated apoptosis, likely representing receptor cleavage and generation of the 4ICD intracellular signaling fragment. In NRG4-treated macrophages, the immunostaining pattern is consistent with 4ICD localization to the mitochondria (FIG. 9C), where mitochondrial-mediated apoptosis may be the mode of action. Relative levels of the receptor may play a role, or differential expression of intracellular chaperones regulating localization of 4ICD (cytoplasm vs. nucleus vs. mitochondria) may be involved. Furthermore, ErbB4 has several splice variants that can contribute to differences in signaling outcomes. For example, the cytoplasmic domain variant CYT1 has SH2 binding sites to elicit PI3K signaling, whereas CYT2 variants do not. Using fibroblasts to compare isoform specific responses, the Elenius group has shown that ErbB4 can both promote either cell survival or cell death under alternative contexts. Further studies will be necessary to evaluate the relative roles of splicing, environmental context, and other interacting pathways in the signaling outcome in macrophages.

Innate inflammation generated by macrophages has largely been thought of as a self-limiting process. However, it is becoming clear that resolution of mucosal inflammation is an active process. Thus understanding the mechanisms that resolve inflammation has emerged as a key question in this field. Mechanisms driving clearance of macrophages are not well understood. In chronic inflammation, these cells are continually replenished by recruitment from circulation, which can create a feed-forward loop. One aspect that may contribute to chronic inflammation is a failure of appropriate self-termination of these cells. In colitis, NRG4 expression is inhibited, leading to an incomplete or altered ErbB4 signaling circuit. Here, we extended our previous findings by showing this loss of NRG4 occurs early in a model of acute colitis, and NRG4 levels are negatively correlated with TNF expression (FIG. 12A-12H). Replacement of lost NRG4 with exogenous administration following induction of injury in DSS colitis to complete this circuit significantly attenuated inflammation and reduced colonic macrophage numbers (FIG. 12A-12H). ErbB4 expression was undetectable in bone marrow-derived dendritic cells and neutrophils (FIG. 1A-1F). Since macrophages are the only myeloid cells on which we detected ErbB4 expression, together with our NRG4 rescue experiment results these findings support the idea that ErbB4 signaling in macrophages is an anti-inflammatory feedback mechanism in colitis. It is possible that down-regulation of NRG4 may be necessary for a maximal innate immune response to a challenge, and defects in re-expression may contribute to chronic colitis. Future studies to identify the key cellular source of NRG4 in the colon and how its expression is regulated will provide insight into a possible mechanism underlying chronic colitis. Furthermore, as macrophages are early responding cells that shape the development of the immune response, long-term in vivo studies will be required to understand how ErbB4 loss in macrophages impacts adaptive immunity and potentially alters local factors, such as the microbiota, in ways that may be involved in colitis development and resolution.

In summary, our data indicate that ErbB4 is induced on macrophages during inflammation as a mode of feedback inhibition. ErbB4 activation elicits clearance of inflammatory macrophages and promotes recovery. Administration of exogenous NRG4, or identifying other methods to activate ErbB4 signaling in these cells, is a potential approach to alleviate disease in IBD patients and other patients with chronic, macrophage-dependent inflammation. Furthermore, the opposing roles for ErbB4 signaling in different cell types—supporting epithelial survival while triggering macrophage apoptosis—suggest a coordinated pro-recovery role for ErbB4 signaling in the face of injury and inflammation.

Various embodiments of the invention are described above. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for treating a disease-state associated with presence of increased number of ErbB4+ pro-inflammatory macrophages in a subject in need thereof comprising:
   administering a therapeutically effective amount of an activator of ErbB4, wherein the ErbB4 activator is Neuregulin-4, to the subject so as to treat the disease-state in the subject, wherein the disease-state is any one or more of acute lung injury, liver fibrosis, chronic obstructive pulmonary disease, atherosclerosis, radiation therapy-induced intestinal injury, type I diabetes, NASH, gastroenteritis or urinary tract infections.

2. The method of claim 1, wherein the disease-state is acute lung injury.

3. The method of claim 1, wherein the subject has an increased number of ErbB4$^+$ pro-inflammatory macrophages and has been diagnosed with acute lung injury.

4. The method of claim 1, wherein the activator of ErbB4 is administered orally, via inhalation, intravenously, intramuscularly, intraperitoneally, orally, by enema or via inhalation.

5. The method of claim 1, wherein the effective amount of the activator of ErbB4 is an amount that induces apoptosis of ErbB4+ pro-inflammatory macrophages.

6. The method of claim 1, wherein the effective amount of the ErbB4 activator is about 0.001-0.005 mg/kg, 0.005-0.01 mg/kg, 0.01-0.02 mg/kg, 0.02-0.04 mg/kg, 0.04-0.06 mg/kg, 0.06-0.08 mg/kg, 0.08-1 mg/kg, 1-5 mg/kg, 5-10 mg/kg, 5-7 mg/kg, 6-7 mg/kg, 6-8 mg/kg, 7-8 mg/kg, 7-10 mg/kg, 10-15 mg/kg, 15-20 mg/kg, 20-25 mg/kg, 25-30 mg/kg, 30-35 mg/kg, 35-40 mg/kg, 40-45 mg/kg, 45-50 mg/kg, 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg, 900-1000 mg/kg, 1000-1100 mg/kg, 1100-1200 mg/kg, 1200-1300 mg/kg, 1300-1400 mg/kg, 1400-1500 mg/kg, 1500-1600 mg/kg, 1600-1700 mg/kg, 1700-1800 mg/kg, 1800-1900 mg/kg, 1900-2000 mg/kg, 2000-2100 mg/kg, 2100-2200 mg/kg, 2200-2300 mg/kg, 2300-2400 mg/kg, 2400-2500 mg/kg, 2500-2600 mg/kg, 2600-2700 mg/kg, 2700-2800 mg/kg, 2800-2900 mg/kg or 2900-3000 mg/kg.

7. The method of claim 1, wherein the increased number of ErbB4$^+$ macrophages is an increase relative to reference value.

8. The method of claim 7, wherein the reference value is the mean or median number of ErbB4$^+$ macrophages in a normal subject.

9. The method of claim 7, wherein the reference value is the mean or median number of ErbB4$^+$ macrophages in subjects that have been diagnosed and successfully treated for the disease-state.

* * * * *